United States Patent
Keller et al.

(10) Patent No.: US 10,077,428 B2
(45) Date of Patent: Sep. 18, 2018

(54) HUMAN CARDIOVASCULAR PROGENITOR CELLS

(75) Inventors: Gordon Keller, Toronto (CA); Lei Yang, New York, NY (US); Steven Kattman, Toronto (CA)

(73) Assignee: ICAHN SCHOOL OF MEDICINE AT MOUNT SINAI, New York, NY (US)

(*) Notice: Subject to any disclaimer, the term of this patent is extended or adjusted under 35 U.S.C. 154(b) by 1009 days.

(21) Appl. No.: 12/410,782

(22) Filed: Mar. 25, 2009

(65) Prior Publication Data
US 2009/0269314 A1    Oct. 29, 2009

Related U.S. Application Data

(60) Provisional application No. 61/040,049, filed on Mar. 27, 2008.

(51) Int. Cl.
C12N 5/077 (2010.01)
A61K 35/12 (2015.01)

(52) U.S. Cl.
CPC ............ *C12N 5/0657* (2013.01); *A61K 35/12* (2013.01); *C12N 2501/115* (2013.01); *C12N 2501/155* (2013.01); *C12N 2501/16* (2013.01); *C12N 2501/165* (2013.01); *C12N 2501/415* (2013.01); *C12N 2506/02* (2013.01)

(58) Field of Classification Search
CPC ............ C12N 5/0657; C12N 2501/115; C12N 2501/155; A61K 35/12
See application file for complete search history.

(56) References Cited

U.S. PATENT DOCUMENTS

| | | |
|---|---|---|
| 6,491,912 B2 | 12/2002 | Dinsmore |
| 7,452,718 B2 * | 11/2008 | Gold et al. ............ 435/377 |
| 2005/0043260 A1 | 2/2005 | Schneider et al. |
| 2005/0164382 A1 | 7/2005 | Xu |
| 2005/0021439 A1 | 9/2005 | Gold et al. |
| 2005/0214939 A1 * | 9/2005 | Gold et al. ............ 435/366 |
| 2010/0158872 A1 * | 6/2010 | Keller et al. ............ 424/93.7 |

FOREIGN PATENT DOCUMENTS

| | | |
|---|---|---|
| WO | 2003/035838 A2 | 5/2003 |
| WO | 2007/002385 A2 | 1/2007 |
| WO | WO2007/002136 | 1/2007 |
| WO | WO2007/002358 | 1/2007 |

OTHER PUBLICATIONS

Kattman et al Cell. 2006, 11, 723-732.*
Kattman et al Trends Cardiovasc Med 2007;17:240-246.*
Johansson et al (Molecular and Cell Biology, Jan. 1995, p. 141-151.*
Yang et al Nature, 2008, 524-529.*
Ema et al. (2006) Blood 107:111-117.*
Yamashita et al. (2005) FASEB 19:1534-1536.*
Thomson et al. (Science 282:1145, 1998.*
Ireland KA., Visualizing Human Biology, 3rd Ed., Wiley and Sons Inc., 2008, p. 527.*
Reubinoff et al. (2000, Nature Biotechnology, vol. 18, pp. 399-404.*
Reijo et al. (Differentiation, 2009, vol. 78, pp. 18-23.*
Pant et al., 2009, Cloning and Stem Cells, vol. 11(3), pp. 355-365.*
Van Pavert et al. Mol Reprod Dev. Aug. 2001;59(4):390-9, abstract only , p. 1.*
Yang et al Nature 453, 524-528, 2008.*
Gouon-Evans (Nature Biotechnology 24, 1402-1411, 2006).*
Ware et al. 2014, PNAS, vol. 111(12), pp. 4484-4489.*
U.S. Appl. No. 11/993,688, Keller et al.
Chen et al. (2008) *Nature Biotechnology* 26:1169.
Dalton et al. (2008) *Regen. Med.* 3:181.
Garry et al. (2006) *Cell* 127:1101.
Kattman et al. (2007) *TCM* 17:240.
Kattman et al. (2006) *Developmental Cell* 11:723.
Keller et al. (2007) "Lineage Specific Differentiation of Embryonic Stem Cells," 2nd Annual Wisconsin Stem Cell Symposium: Heart & Blood.
Kokubo et al. (2004) *Developmental Biology* 278:3001.
LaFlamme et al. (2007) *Nature Biotechnology* Advance Online Publication, 1-10.
Moretti et al. (2006) *Cell* 127:1151.
Murray et al. (2008) *Cell* 132:680.
Lawson et al. (2001) *Development* 128:3675.
Nemir et al. (2006) *Circ. Res.* 98:1471.
Nostro et al. (2008) *Cell Stem Cell* 2:60.
Snir et al. (2003) *Am. J. Physiol. Circ. Physiol.* 285:H2355.
Rosenblatt-Velin et al. (2005) *Journal of Clinical Investigation* 115:1724-1733.
Messina Elisa et al: "Isolation and expansion of adult cardiac stem cells from human and murine heart", Circulation Research, vol. 95, No. 9, Oct. 29, 2004, pp. 911-921, XP002477755, American Heart Association, Inc., US.
Goumans M J et al: "TGF-beta1 induces efficient differentiation of human cardiomyocyte progenitor cells into functional cardiomyocytes in vitro", Stem Cell Research, Elsevier, NL, vol. 1, No. 2, Mar. 12, 2008, pp. 138-149, XP022764784.
Goumans M J et al: "TGF-beta1 induces efficient differentiation of human cardiomyocyte progenitor cells into functional cardiomyocytes in vitro", Stem Cell Research, Elsevier, NL, vol. 1, No. 2, Mar. 12, 2008, pp. 1-11, XP002660160.
E. M. F. Van Craenenbroeck et al: "A maximal exercise bout increases the number of circulating CD34+/KDR+ endothelial progenitor cells in healthy subjects. Relation with Lipid profile", Journal of Applied Physiology, vol. 104, No. 4, Jan. 24, 2008, pp. 1006-1013, XP055008241.

(Continued)

*Primary Examiner* — Anoop Kumar Singh
(74) *Attorney, Agent, or Firm* — Fox Rothschild LLP

(57) ABSTRACT

The present invention provides populations of human cardiovascular progenitor cells, methods of making such cells, and methods of using the cells for production of populations of cardiovascular colonies and populations of cardiomyocytes. Methods of cardiomyocytes replacement therapy are also provided.

5 Claims, 32 Drawing Sheets

Specification includes a Sequence Listing.

(56) References Cited

OTHER PUBLICATIONS

G. P. Fadini et al: "Peripheral Blood CD34+KDR+ Endothelial Progenitor Cells Are Determinants of Subclinical Atherosclerosis in a Middle-Aged General Population", Stroke, vol. 37, No. 9, Sep. 1, 2006, pp. 2277-2282, XP055008242.
Takahashi, et al. "Induction of Pluripotent Stem Cells from Adult Human Fibroblasts by Defined Factors." Cell 131: 861-872. (2007).

* cited by examiner

HUMAN CARDIOVASCULAR PROGENITOR CELLS

CROSS-REFERENCE TO RELATED APPLICATION

This application claims the benefit of U.S. Provisional Application No. 61/040,049 filed Mar. 27, 2008.

STATEMENT REGARDING FEDERALLY SPONSORED RESEARCH

This invention was made with government support under grant numbers HL071800 and GM075019 awarded by the National Institutes of Health. The government has certain rights in the invention.

BACKGROUND OF THE INVENTION

During embryonic development, the tissues of the body are formed from three major cell populations: ectoderm, mesoderm and definitive endoderm. These cell populations, also known as primary germ cell layers, are formed through a process known as gastrulation. Following gastrulation, each primary germ cell layer generates a specific set of cell populations and tissues. Mesoderm gives rise to blood cells, endothelial cells, cardiac and skeletal muscle, and adipocytes. Definitive endoderm generates liver, pancreas and lung. Ectoderm gives rise to the nervous system, skin and adrenal tissues. The process of tissue development from these germ cell layers involves multiple differentiation steps, reflecting complex molecular changes. With respect to mesoderm and its derivatives, three distinct stages have been defined. The first is the induction of mesoderm from cells within a structure known as the epiblast. The newly formed mesoderm, also known as nascent mesoderm, migrates to different positions that will be sites of future tissue development in the early embryo. This process, known as patterning, entails some molecular changes that are likely reflective of the initial stages of differentiation towards specific tissues. The final stage, known as specification, involves the generation of distinct tissues from the patterned mesodermal subpopulations.

Evidence suggests that mesoderm is induced in successive waves which represent subpopulations with distinct developmental potential. The mesoderm that is formed first migrates to the extraembryonic region and gives rise to hematopoietic and endothelial cells, whereas the next population migrates anteriorly in the developing embryo and contributes to the heart and cranial mesenchyme. These lineage relationships were defined initially through histological analysis and have been largely confirmed by cell tracing studies. With respect to hematopoietic commitment, there is now compelling evidence from studies with the ES cell differentiation model and on the mouse embryo that the earliest identifiable progenitor is a cell that also displays vascular potential, a cell that is known as the hemangioblast (Choi et al. (1998); Development 125:725-732; Huber et al. (2004) Nature 432:625-30). Analysis of this progenitor revealed that it co-expresses the mesoderm gene brachyury and the receptor tyrosine kinase Flk-1, indicating that it represents a subpopulation of mesoderm undergoing commitment to the hematopoietic and vascular lineages (Fehling et al. (2003) Development 130:4217-4227). Lineage-tracing studies have demonstrated that the heart develops from a Flk-1$^+$ population, suggesting that a comparable multipotential cell may exist for the cardiovascular system (Ema et al. (2006) Blood 107:111-117). Analyses of ES cell differentiation cultures have provided evidence for the existence of a Flk-1$^+$ progenitor with cardiac and endothelial potential (Yamashita et al. (2005) FASEB 19:1534-1536). Recent studies also support the existence of murine cardiovascular progenitors that may give rise to multiple cardiovascular lineages. (Kattman et al. (2006) Dev. Cell 11:723-732; Moretti et al. (2006) Cell 127:1151-1165; Wu et al. (2006) Cell 127:1137-1150). A human cardiovascular progenitor population has not heretofore been identified.

SUMMARY OF THE INVENTION

The present invention provides enriched populations of human cardiovascular progenitor cells. The human cardiovascular progenitor cells are characterized by the presence of the cell surface marker KDR and the absence of the cell surface marker C-KIT. The human cardiovascular progenitor cells are capable of differentiating into cardiomyocytes, endothelial cells and vascular smooth muscle cells in vitro and in vivo.

In another embodiment, the present invention provides methods of producing human cardiovascular progenitor cells from human embryoid bodies (EBs) comprising culturing the EBs in the presence of an activin and a bone morphogenic factor (BMP) and optionally basic Fibroblast Growth Factor (bFGF), and subsequently culturing in the presence of an inhibitor of the Wnt growth factor and optionally vascular endothelial growth factor (VEGF) to provide human cardiovascular progenitor cells, and harvesting the cells from the cell culture.

In another embodiment, the present invention provides a method of generating a population of cells containing at least about 30% and preferably at least about 40%, and more preferably at least about 50% human cardiomyocytes comprising culturing the human cardiovascular progenitor cells in the presence of an inhibitor of Wnt and optionally VEGF. In one embodiment, the cells are cultured as monolayers. In another embodiment, the cells are cultured as aggregates. The presence of cardiomyocytes may be determined by assessing contractile activity of cells or by measuring expression of genes indicative of cardiomyocytes, such as for example cardiac troponin T (CTNT).

The present invention further provides a method of generating human cardiovascular colonies containing cardiomyocytes, endothelial cells and vascular smooth muscle cells comprising culturing the human cardiovascular progenitor cells in the presence of VEGF, bFGF, and an inhibitor of Wnt. In a preferred embodiment, the cells are cultured in methylcellulose.

The human cardiovascular precursor cells and the differentiated cells derived therefrom are useful in methods of screening for agents that affect cardiovascular progenitors, cardiomyocytes, endothelial cells, vascular smooth muscle cells, and cardiovascular tissue.

The human cardiovascular precursor cells are also useful for expansion and storage and as a source of cardiomyocytes, endothelial cells and vascular smooth muscle cells.

The human cardiovascular precursor cells and the differentiated cells derived therefrom are also useful in methods of improving or reconstituting cardiac function in a mammal, and for engineering cardiovascular tissue in vitro for transplantation.

DETAILED DESCRIPTION OF THE INVENTION

Figure 1:
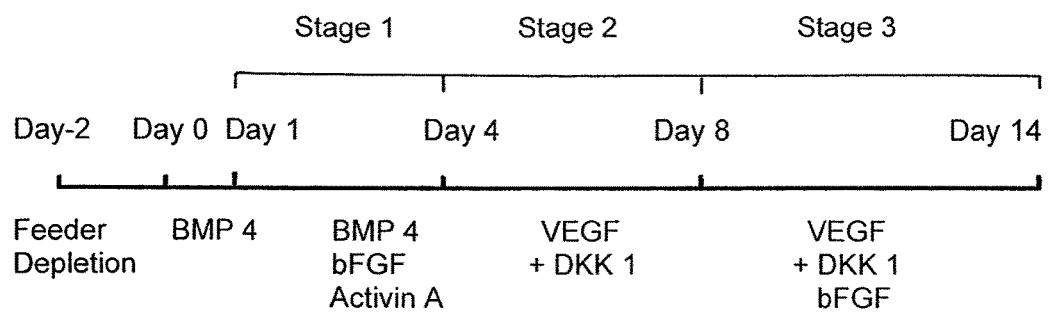
FIG. 1 is an outline of a protocol used to direct differentiation of human embryonic stem cells (hESC) to the cardiac lineage in accordance with one embodiment of the present invention.

The present invention provides populations of human cardiovascular progenitor cells. The human cardiovascular progenitor cells of the present invention are capable of differentiation, under appropriate conditions, into cardiomyocytes, endothelial cells, and vascular smooth muscle cells. The human cardiovascular progenitor cells are characterized by the expression of the tyrosine kinase receptor KDR and by the lack of expression of the tyrosine kinase receptor C-KIT.

In one embodiment of the invention, the human cardiovascular progenitor cells a r e obtained from embryoid bodies (EBs). EBs are three dimensional colonies that contain developing populations from a broad spectrum of lineages. Conditions for formation of EBs from embryonic stem cells (ESC) are known in the art. For example, human ESC maintained on embryonic feeder cells may be depleted of feeders, for example by culturing on a layer of basement membrane matrix such as Matrigel™ (BD Biosciences, Bedford, Mass.), dissociated to form small clusters and plated in serum free media in the presence of a BMP. In one preferred embodiment of the invention, feeder-depleted human ESC are cultured in serum free media in the presence of BMP4 for about one day to form EBs. In another preferred embodiment, the concentration of BMP4 is from about 0.1 ng/mL to about 1.0 ng/mL, and more preferably about 0.5 ng/mL.

Human ESC may be obtained commercially or by methods known in the art. For example, human ESC may be prepared from blastocysts by methods known in the art and disclosed for example in U.S. Pat. No. 5,843,780 to Thomson et al. and by Reubinoff et al. (2000) Nature Biotech 18:399.

EBs may also be formed from induced pluripotent stem (iPS) cells by methods known in the art and disclosed, for example, by Takahashi et al. (2007) *Cell* 131:861 and Mali et al. (2008) *Stem Cells* 26:1998.

The human cardiovascular precursor cells of the present invention may be obtained by culturing human EBs in serum free media in the presence of an activin and a BMP, subsequently culturing in the presence of an inhibitor of Wnt to provide a population of cardiovascular progenitor cells, and optionally harvesting the cells from culture and further optionally enriching the harvested cell population for cardiovascular progenitor cells. In preferred embodiments the activin is activin A, the BMP is BMP4, and the inhibitor of Wnt is Dickkopf-1 (DKK-1).

Another embodiment of the present invention provides a method for producing human cardiovascular precursor cells comprising culturing human EBs in serum free media in the presence of activin A and BMP4 and optionally bFGF for about one to about four days, and subsequently culturing the cells in serum free media in the presence of DKK-1 and optionally VEGF for about one to two days, harvesting the population of cells, and optionally enriching the population for human cardiovascular progenitor cells.

In a preferred embodiment the EBs are cultured in the presence of activin A and BMP4 and optionally bFGF for about four days. The concentrations of activin A, BMP4 and optionally bFGF are sufficient to induce a primitive streak-like population of cells characterized by the upregulation of expression of T and WNT3A. In the subsequent step, the concentrations of DKK-1 and optionally VEGF are sufficient to provide a population of cardiovascular progenitor cells.

In a preferred embodiment, the concentration of activin A is from about 0.5 ng/mL to about 30 ng/mL, and more preferably from about 1.0 ng/mL to about 5.0 ng/mL. In a most preferred embodiment the concentration of activin A is about 3.0 ng/mL.

In a preferred embodiment, the concentration of BMP4 is from about 1.0 ng/mL to about 20.0 ng/mL, and more preferably from about 5.0 ng/mL to about 15 ng/mL. In a most preferred embodiment, the concentration of BMP4 is about 10 ng/mL.

In a preferred embodiment, the concentration of bFGF is from about 1.0 ng/mL to about 10.0 ng/mL, and more preferably from about 3.0 ng/mL to about 6.0 ng/mL. In a most preferred embodiment, the concentration of bFGF is about 5.0 ng/mL.

In a preferred embodiment, the concentration of DKK1 is from about 100 ng/mL to about 200 ng/mL, and more preferably from about 125 ng/mL to about 175 ng/mL. In a most preferred embodiment, the concentration of DKK1 is about 150 ng/mL.

In another preferred embodiment, the concentration of VEGF is from about 1.0 ng/mL to about 50.0 ng/mL, and more preferably from about 1.0 ng/mL to about 25.0 ng/mL. In a most preferred embodiment, the concentration of VEGF is about 10.0 ng/mL.

In another preferred embodiment of the present invention, human EBs are cultured in serum free media for about four days in the presence of about 3.0 ng/mL of activin A, about 10.0 ng/mL of BMP4 and about 5.0 ng/mL of bFGF, at which time about 150 ng/mL of DKK1 and about 10.0 ng/mL of VEGF are added and cells are cultured for about one to two days to produce cardiovascular progenitor cells. In another preferred embodiment, the population is enriched for cardiovascular progenitor cells, for example by sorting for cells that express KDR and do not express C-KIT. In a preferred embodiment, the sorting is by immunoselection, for example by flow cytometry.

In another embodiment, the present invention provides a method of generating a population of human cardiomyocytes comprising culturing the human cardiovascular progenitor cells in the presence of an inhibitor of Wnt and optionally VEGF for about seven to about 10 days, and harvesting a population of human cardiomyocytes from culture. In a preferred embodiment, the inhibitor of Wnt is DKK1, and the preferred concentrations of DKK1 and VEGF are as described hereinabove. In one preferred embodiment, the cells are plated as monolayers in gelatin-coated wells. In another embodiment, the cells are cultured in low cluster dishes as aggregates. The populations of human cardiomyocytes contain at least about 30%, and preferably at least about 40%, and more preferably at least about 50% cardiomyocytes. In other embodiments, the populations of human cardiomyocytes contain at least about 70%, and preferably at least about 80% and more preferably at least about 90% and up to 100% cardiomyocytes. The cardiomyocytes may be identified by assessing contractile activity or by measuring expression of genes indicative of cardiomyocytes, such as for example CTNT.

The human cardiovascular progenitor cells of the present invention are also useful for generating subpopulations of cardiomyocytes including, for example, atrial, ventricular, and pacemaker cells, using differentiation conditions known to those of skill in the art.

In another embodiment, the present invention provides a method of generating cardiovascular colonies containing cardiomyocytes, endothelial cells, and vascular smooth muscle cells comprising culturing the human cardiovascular precursor cells in the presence of VEGF, bFGF and an inhibitor of Wnt, preferably DKK1, for about three to about seven days. In a preferred embodiment, the cells are plated in methylcellulose. The preferred concentrations of VEGF, bFGF and DKK are as described hereinabove. The presence of cardiomyocytes, endothelial cells, and vascular smooth muscle cells can be determined by measuring expression of genes indicative of cardiomyocytes, such as CTNT, and genes indicative of endothelial cells, such as CD31, VE-CADHERIN and genes indicative of vascular smooth muscle cells, such as SMA and CALPONIN.

The present invention further provides methods for screening for agents that have an effect on human cardiovascular progenitor cells, cardiovascular colonies, cardiomyocytes, endothelial cells and vascular smooth muscle cells. The method comprises contacting cells from one of the cell populations described hereinabove with a candidate agent, and determining whether the agent has an effect on the cell population. The agent to be tested may be natural or synthetic, one compound or a mixture, a small molecule or polymer including polypeptides, polysaccharides, polynucleotides and the like, an antibody or fragment thereof, a compound from a library of natural or synthetic compounds, a compound obtained from rational drug design, a condition such as a cell culture condition, or any agent the effect of which on the cell population may be assessed using assays known in the art. The effect on the cell population may be determined by any standard assay for phenotype or activity, including for example an assay for marker expression, receptor binding, contractile activity, electrophysiology, cell viability, survival, morphology, or DNA synthesis or repair. Standard proliferation and differentiation assays are described in U.S. Pat. No. 6,110,739. Such agents are useful for the control of cell growth, differentiation and survival in vivo and in vitro, and tissue maintenance, regeneration and repair.

The present invention further provides compositions comprising populations of human cardiovascular precursor cells and compositions comprising populations of human cardiovascular colonies. The compositions may comprise pharmaceutically acceptable carriers and diluents. The compositions may further comprise components that facilitate engraftment. Compositions comprising these populations are useful for cell and tissue replacement and repair, and for generating populations of cardiomyocytes, endothelial cells, and vascular smooth muscle cells in vitro and in vivo. Compositions comprising human cardiovascular progenitor cells are useful for expansion of the progenitor populations. The compositions may be formulated as a medicament or delivery device for treating a cardiac condition.

In another embodiment, the present invention provides methods of cell replacement and methods of tissue replacement useful for treatment of disorders characterized by insufficient cardiac function including, for example, congenital heart disease, coronary heart disease, cardiomyopathy, endocarditis and congestive heart failure. Both the differentiated cells and the cardiovascular progenitor cells are useful for replacement therapy, since the progenitor populations are capable of differentiation to the cardiomyocyte, endothelial and vascular smooth muscle lineages in vivo. The cells are also useful for generating cardiovascular tissue in vitro. Methods for engineering cardiac tissue are known in the art and reviewed for example by Birla in "Stem Cell Therapy and Tissue Engineering for Cardiovascular Repair" Springer, 2006.

Accordingly, in one embodiment the present invention provides a method of cardiomyocyte replacement therapy comprising administering to a subject in need of such treatment a composition comprising cardiomyocytes isolated from a cell population enriched for human cardiovascular progenitor cells obtained in accordance with the present invention. In another embodiment, the present invention provides a method of treating a disorder characterized by insufficient cardiac function comprising administering to a subject in need of such treatment a composition comprising human cardiovascular progenitor cells. In a preferred embodiment, the subject is a human. The composition may be administered by a route that results in delivery to or migration to cardiac tissue including, for example, injection or implantation, and under conditions that result in a reduction of at least one adverse effect or symptom or the disorder.

All references cited herein are incorporated herein in their entirety.

The following examples serve to further illustrate the present invention.

Example 1

Materials and Methods

Maintenance of Human ES Cells

H1 (NIH code WA01) from WiCell Research Institute (Madison, Wis.) and hES2 (NIH code ES02) from ESI International (Singapore) were maintained on irradiated mouse embryonic feeder cells in hESC media consisting of Dulbecco's Modified Eagle Medium (DMEM)/F12 (50:50; Mediatech, Herndon, Va.) supplemented with 20% knock-out serum replacement (SR), 100 µM nonessential amino acids, 2 mM glutamine, 50 U/mL penicillin, 50 µg/mL streptomycin (Invitrogen, Grand Island, N.Y.), $10^{-4}$ M β-mercaptoethanol (Sigma, St Louis, Mo.) and 20 ng/mL hbFGF (R&D Systems, Minneapolis, Minn.) in 6-well tissue culture plates. The AAVS1-targeted hES2 cell line was generated by co-infection of parental hES2 cells with $10^6$ viral particles of both, AAV2-TRUF11 (CAG-GFP-TK-neo) and wild type AAV2. After G418 selection, GFP positive cells were sorted and subclones were isolated. Targeted integration of the transgenes was confirmed by ligation-mediated polymerase chain reaction (LM PCR). Wild type AAV sequences were not detected in GFP positive clones. RFP expressing hES cells were generated by targeting the RFP cDNA to the Rosa26 locus of hES2 cells as described by Irion et al. (2007) Nat. Biotechnol. 12:1477-1482.

Differentiation of Human ES Cells

Prior to the generation of EBs, hESCs were cultured on a layer of Matrigel (BD Biosciences, Bedford, Mass.) to deplete the feeders for 48 hours. Cells from the Matrigel culture were dissociated to small clusters by 20-minute treatment with collagenase B (1 mg/mL; Roche, Indianapolis, Ind.) followed by a 2-minute treatment with trypsin-EDTA (0.05%). From day 0-1, EBs were plated in 2 mL basic media (StemPro-34 (Invitrogen), 2 mM glutamine, $4\times10^{-4}$ M monothioglycerol (MTG), and 50 µg/mL ascorbic acid (Sigma) plus 0.5 ng/mL BMP4 (R&D Systems). The following concentrations of factors were used for EB formation, mesoderm induction and cardiac specification: BMP4:10 ng/mL, hbFGF: 5 ng/mL, ActivinA: 3 ng/ml, hDKK1:150 ng/mL, hVEGF: 10 ng/mL. The factors were added with the following sequence: day 1-4, BMP4, hbFGF and ActivinA; day 4-8, VEGF and DKK1; following day 8, VEGF, DKK1, and bFGF. The medium was changed every 4 days beyond day 8. All human factors and inhibitors were purchased from R&D Systems (Minneapolis, Minn.). Cultures were maintained in a 5% $CO_2$, 5% $O_2$, and 90% $N_2$ environment for the first 10-12 days of culture and then in 5% $CO_2$/air environment for the following days.

Flow Cytometry Sorting and Tube Formation on Matrigel

EBs were harvested and dissociated to single cells with trypsin (0.25% trypsin-EDTA). Following trypsinization, analyses were carried out using Facscalibur flow cytometer (Becton Dickinson). Cells were sorted using a MoFlo (Dako Cytomation, Fort Collins, Colo.) cell sorter. Flow cytometric data were analyzed using the FlowJo (Treestar, San Carlos, Calif.) software programs. Anti-KDR-PE, anti-C-KIT-APC were purchased from R&D Systems. Sorted $KDR^{low}$/C-$KIT^{neg}$ population was differentiated in Stempro34 medium supplemented with VEGF (25 ng/ml) and bFGF (25 ng/ml). Tube-like structures were formed within 24 hours after transferred to Matrigel-coated glass coverslips.

Immunofluorescence

Dissociated cells were cultured on glass cover slips for 2 days. At this point the cells were fixed with 4% PFA and then stained. The following antibodies were used for immunostaining: Anti-human CD31, anti-human VE-Cadherin from R&D Systems, anti-mouse Troponin T and anti-human Smooth Muscle Actin from Lab Vision (Freemont, Calif.), anti-human ANP, Connexin 43 and anti-human α/β MHC antibodies from Chemicon (Temecula, Calif.), and anti-human α-Actinin from Sigma (St. Louis, Mo.). Anti-human smooth muscle myosin heavy chain (SMHC), Caldesmon, Von Willebrand Factor antibodies were purchased from DakoCytomation (Carpinteria, Calif.). The Cy2, Cy3 and Cy5 conjugated second antibodies were obtained from Jackson ImmunoResearch (West Grove, Pa.). Fluorescence was visualized using a Leica DMRA2 fluorescence microscope (Leica, Wetzlar, Germany), and images were recorded using a digital Hamamatsu CCD camera (Hamamatsu City, Japan).

Colony Assays

To generate cardiovascular colonies, $KDR^{low}$/$C\text{-}KIT^{neg}$ cells isolated from day 6 EBs were aggregated in the presence of VEGF (25 ng/mL), bFGF (10 ng/ml) and DKK1 (150 ng/ml) for 2-3 days. At this stage, the aggregates were dissociated and the cells were cultured in methylcellulose containing VEGF (25 ng/mL), bFGF (25 ng/ml) and DKK1 (150 ng/ml) in a 5% $CO_2$, 5% $O_2$, and 90% $N_2$ environment. Colonies were scored following 4-6 days of cultures for the colony frequency analysis.

RT-PCR

For expression studies, individual colonies were isolated from the methylcellulose cultures and analyzed using a modified version of the protocol previously described by Brady et al. (1993) Methods Enzymol. 225:611-623. The amplified cDNA was then subjected to normal PCR. Real-time quantitative PCR was performed on the MasterCycler EP RealPlex (Eppendort). Experiments were done in triplicate using Platinum SYBR GreenER qPCR SuperMix (Invitrogen). All primers are described in Table I. All annealing reactions were carried out at 60° C.

TABLE 1

| GENE | FORWARD PRIMER | REVERSE PRIMER |
|---|---|---|
| Primers for Normal PCR | | |
| T(Brachyury) | tgt ccc agg tgg ctt aca gat gaa (SEQ ID NO: 1) | ggt gtg cca aag ttg cca ata cac (SEQ ID NO: 2) |
| WNT3A | aat gcc act gca tct tcc act ggt (SEQ ID NO: 3) | tgg tga cag ttc ctt gct gtc tga (SEQ ID NO: 4) |
| DKK1 | tct cag tgt ggc act tac ctg t (SEQ ID NO: 5) | cca aga gat cct tgc gtt cta gac t (SEQ ID NO: 6) |
| KDR | cct cta ctc cag taa acc tga ttg gg (SEQ ID NO: 7) | tgt tcc cag cat ttc aca cta tgg (SEQ ID NO: 8) |
| ISL1 | cac aag cgt ctc ggg att gtg ttt (SEQ ID NO: 9) | agt ggc aag tct tcc gac aa (SEQ ID NO: 10) |
| NKX2.5 | gcg att atg cag cgt gca atg agt (SEQ ID NO: 11) | aac ata aat acg ggt ggg tgc gtg (SEQ ID NO: 12) |
| TBX20 | gaa aga cca cac agc ctc att gct (SEQ ID NO: 13) | tca atg tca gtg agc ctg gag gaa (SEQ ID NO: 14) |
| GFP | ttc tcg gcc aca agc tgg aat aca (SEQ ID NO: 15) | act ggg tgg aca ggt aat ggt tgt (SEQ ID NO: 16) |
| RFP | acc tgg tgg agt tca aga cca tct (SEQ ID NO: 17) | acc tct aca aat gtg gta tgg ctg (SEQ ID NO: 18) |
| CD31 | atc att tct agc gca tgg cct ggt (SEQ ID NO: 19) | att tgt gga ggg cga ggt cat aga (SEQ ID NO: 20) |
| β-ACTIN | ttt gaa tga tga gcc ttc gtc ccc (SEQ ID NO: 21) | ggt ctc aag tca gtg tac agg taa gc (SEQ ID NO: 22) |
| Primers for both Normal PCR and QPCR | | |
| OCT4 | aac ctg gag ttt gtg cca ggg ttt (SEQ ID NO: 23) | tga act tca cct tcc ctc caa cca (SEQ ID NO: 24) |
| C-KIT | att ccc ag ccc atg agt cct tga (SEQ ID NO: 25) | aca cgt gga aca cca aca tcc t (SEQ ID NO: 26) |
| CALPONIN | aag gac gca ctg agc aac gct att (SEQ ID NO: 27) | acg cca ctg tca cat cca cat agt (SEQ ID NO: 28) |
| TBX5 | aaa tga aac cca gca tag gag ctg gc (SEQ ID NO: 29) | aca ctc agc ctc aca tct tac cct (SEQ ID NO: 30) |
| CTNT | ttc acc aaa gat ctg ctc ctc gct (SEQ ID NO: 31) | tta tta ctg gtg tgg agt ggg tgt gg (SEQ ID NO: 32) |
| MLC2A | aca tca tca ccc acg gag aag aga (SEQ ID NO: 33) | att gga aca tgg cct ctg gat gga (SEQ ID NO: 34) |
| VE-CAD | tgg aga agt ggc atc agt caa cag (SEQ ID NO: 35) | tct aca atc cct tgc agt gtg ag (SEQ ID NO: 36) |

TABLE 1-continued

| GENE | FORWARD PRIMER | REVERSE PRIMER |
| --- | --- | --- |
| SMA | aat act ctg tct gga tcg gtg gct (SEQ ID NO: 37) | acg agt cag agc ttt ggc tag gaa (SEQ ID NO: 38) |
| NFATC | ttg acc tga act cgt gcc tta gga (SEQ ID NO: 39) | ggc ctt cag gtt gtt tct ttc cgt (SEQ ID NO: 40) |
| NEUD | ccc atg gtg ggt tgt cat ata ttc atg t (SEQ ID NO: 41) | cca gca tca cat ctc aaa cag cac (SEQ ID NO: 42) |
| Primers for QPCR | | |
| CD31 | tct atg acc tcg ccc tcc aca aa (SEQ ID NO: 43) | gaa cgg tgt ctt cag gtt ggt att tca (SEQ ID NO: 44) |
| ISL1 | ttg tac ggg atc aaa tgc gcc aag (SEQ ID NO: 45) | agg cca cac agc gga aac a (SEQ ID NO: 46) |
| NKX2.5 | acc tca aca gct ccc tga ctc t (SEQ ID NO: 47) | ata atc gcc gcc aca aac tct cc (SEQ ID NO: 48) |
| TBX20 | gtc tct cag ctc ctg ggt atc atc tt (SEQ ID NO: 49) | tgt tgc tat gga tgc tgt gct ggt (SEQ ID NO: 50) |
| MEOX1 | tgg aag cgt gtg aag gga ggt (SEQ ID NO: 51) | aag gaa gag ggt gaa ggt ggg att g (SEQ ID NO: 52) |
| NRG1 | agt tca gct cct tcc acc aca ac (SEQ ID NO: 53) | cgt ttc ata ctc ctc atc ctc cac tat cc (SEQ ID NO: 54) |
| PAX6 | tcg aag ggc caa atg gag aag aga ag (SEQ ID NO: 55) | ggt ggg ttg tgg aat tgg ttg gta ga (SEQ ID NO: 56) |
| SOX1 | cct gtg tgt acc ctg gag ttt ctg t (SEQ ID NO: 57) | tgc acg aag cac ctg caa taa gat g (SEQ ID NO: 58) |
| GATA1 | tgt cag taa acg ggc agg tac tca (SEQ ID NO: 59) | ata cca tcc ttc cgc atg gtc agt (SEQ ID NO: 60) |
| SOX17 | agg aaa tcc tca gac tcc tgg gtt (SEQ ID NO: 61) | ccc aaa ctg ttc aag tgg cag aca (SEQ ID NO: 62) |
| FOXA2 | gca ttc cca atc ttg aca cgg tga (SEQ ID NO: 63) | gcc ctt gca gcc aga ata cac att (SEQ ID NO: 64) |
| FOXA3 | ttg gcc atg tcg tca cca ttc tct (SEQ ID NO: 65) | ccc aca ccc taa cca gcc ttt (SEQ ID NO: 66) |
| KDR | act ttg gaa gac aga acc aaa tta tct c (SEQ ID NO: 67) | tgg gca cca ttc cac ca (SEQ ID NO: 68) |
| T | cag tgg cag tct cag gtt aag aag ga (SEQ ID NO: 69) | cgc tac tgc agg tgt gag caa (SEQ ID NO: 70) |
| CYCLOPHININ | gaa gag tgc gat caa gaa ccc atg ac (SEQ ID NO: 71) | gtc tct cct cct tct cct cct atc ttt act t (SEQ ID NO: 72) |

In Vivo Analyses of KDR$^{low}$/C-KIT$^{neg}$-Derived Populations

KDR$^{low}$/C-KIT$^{neg}$ cells derived from GFP expressing hESC were cultured in the presence of VEGF (10 ng/mL), bFGF (10 ng/ml) and DKK1 (150 ng/ml) for 5-10 days before transplantation. NOD/SCID-gamma mice were anesthetized, intubated, and 100,000 donor cells were injected directly into the left ventricular wall in an open-chest procedure. Hearts were harvested 2-11 weeks post surgery, fixed in 1% paraformaldehyde in cacodylate buffer, and vibrotome-sectioned at 300 um. Grafted regions were identified and cryo-sectioned at 10 um. Immuno-histochemistry was done for GFP antibody (Chemicon, AB3080, 1:100; Vector ABC and DAB kits), α-actinin antibody (Sigma, A7811, 1:500; Chemicon AQ300R secondary antibody, 1:20), CD31 antibody (Dako, M0823, 1:50; Vector ABC and DAB kits), and smooth muscle MHC antibody (Biomedical Technologies, BT-562, 1:300; Alexa 555 secondary antibody, 1:200). Confocal images were analyzed for colocalization using ImageJ and Pierre Bourdoncle's plugin with default settings. For evaluation in the murine infarct model, myocardial infarction was induced in SCID beige mice via direct coronary ligation, using techniques described by Rubert et al. (2007) Nature Biotechnol. 25:993-994. Ten to twenty minutes later the mice were injected with 500,000 KDR$^{low}$/C-KIT$^{neg}$-derived cells (n=9) or an equivalent volume of serum free cell media (n=12). All injections were attempted in the border zone of the infarct. Two weeks later assessment of ventricular function was performed using 9.4 Tesla Magnetic Resonance Imaging.

Patch Clamp

Figure 4:
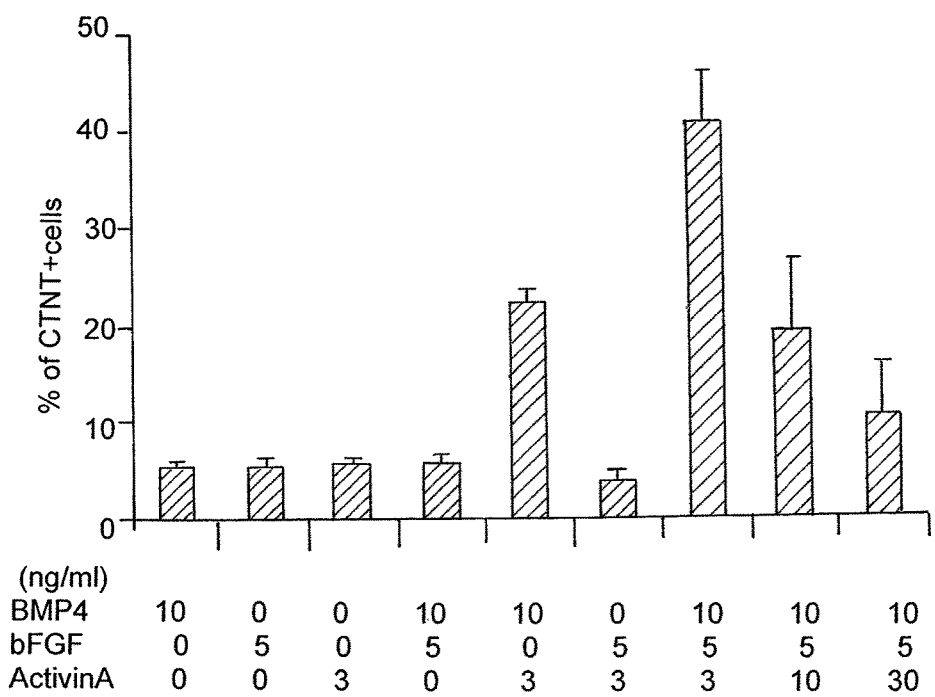
FIG. 4 shows the frequency of CTNT+ cells in day 14 EBs following culture in combinations of BMP4, activin A and bFGF during the induction stage.

Whole cell patch clamp recordings were performed at room temperature using an IX50 inverted microscope (Olympus), a Multiclamp 700A Amplifier, a Digidata 1300 Analogue/Digital converter and a PC with pClamp9.1 software (Axon Instruments, Foster City, Calif.). Bath solution was (in mM): NaCl 136, KCl 4, CaCl$_2$ 1, MgCl$_2$ 2, CoCl$_2$ 5, HEPES10, glucose 10, and tetrodotoxin (TTX) 0.02 (pH 7.4). Pipettes were of 3-5 $_M$'Ω resistance when filled with intracellular solution containing (in mM): KCI 135, EGTA 10, HEPES10, and glucose 5 (pH 7.2). Cells were stepped from a holding potential of −80 mV to test potentials from −80 mV to +40 mV in 20 mV increments, before a −30 mV tail pulse (durations as in FIG. 4). Data were analyzed using pClamp9.1 software (Axon Instruments). Current amplitudes were normalized to cell size (whole-cell membrane capacitance). Inactivation τ values were calculated using a single exponential fit of current decay.

Field Potential Recording

KDR$^{low}$/C-KIT$^{neg}$ cells isolated from day 6 EBs were cultured in the MEA (Multi ChannelSystems) dish with StemPro-34 plus 10 ng/mL VEGF and 150 ng/mL DKK1 for 2-4 weeks. 2 days before recording, cells were changed to DMEM (Cell grow) with 15% FBS. Extracellular electrical activity was simultaneously recorded from 60 channels and analyzed with software MC Rack (Multi Channel Systems).

Example 2

Regulation of Cardiac Development in hESC Differentiation Cultures

Figure 2:
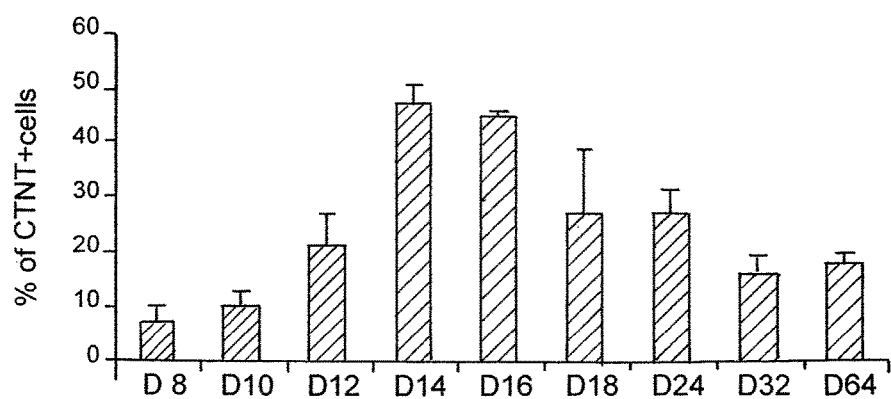
FIG. 2 shows the kinetics of CTNT+ cell development in EBs induced with a combination of BMP4, bFGF and activin A. EBs were harvested at the indicated time points and analyzed by intracellular flow cytometry for the frequency of cells expressing CTNT.
Figure 6:
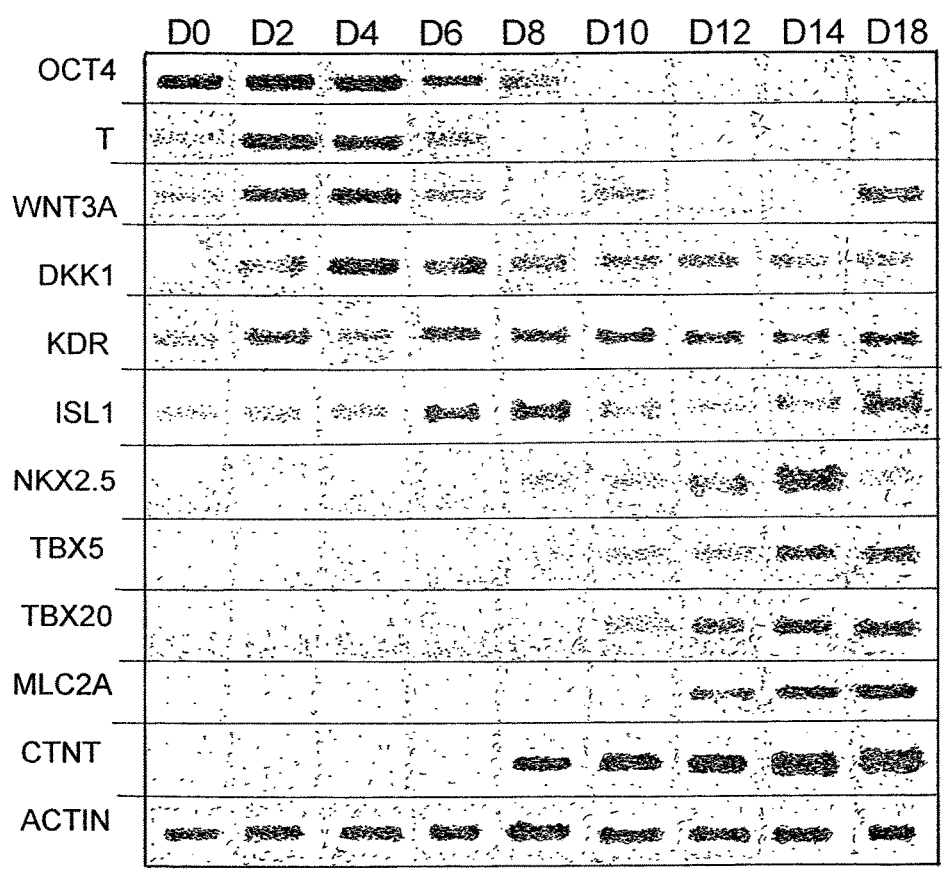
FIG. 6 shows gene expression analysis of EBs at different stages of development.
Figure 20:
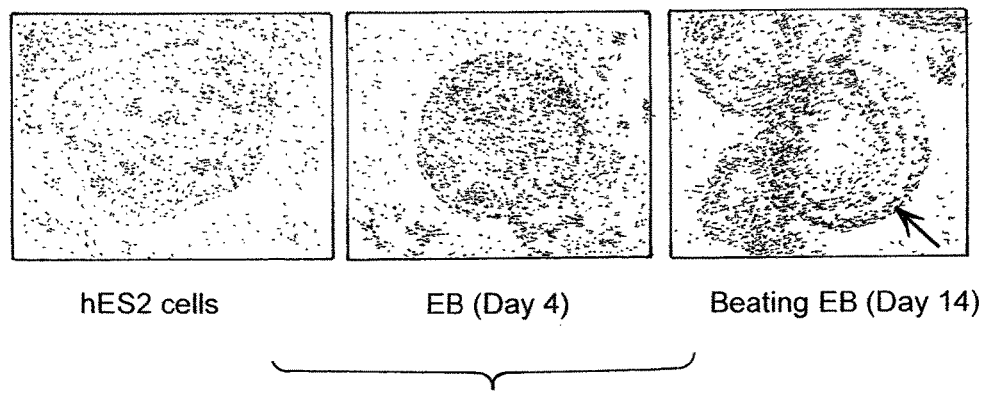
FIG. 20 shows images of undifferentiated hES2 cells, day 4 EBs and day 14 EBs with contracting cardiomyocytes (magnification×200).
Figure 21:
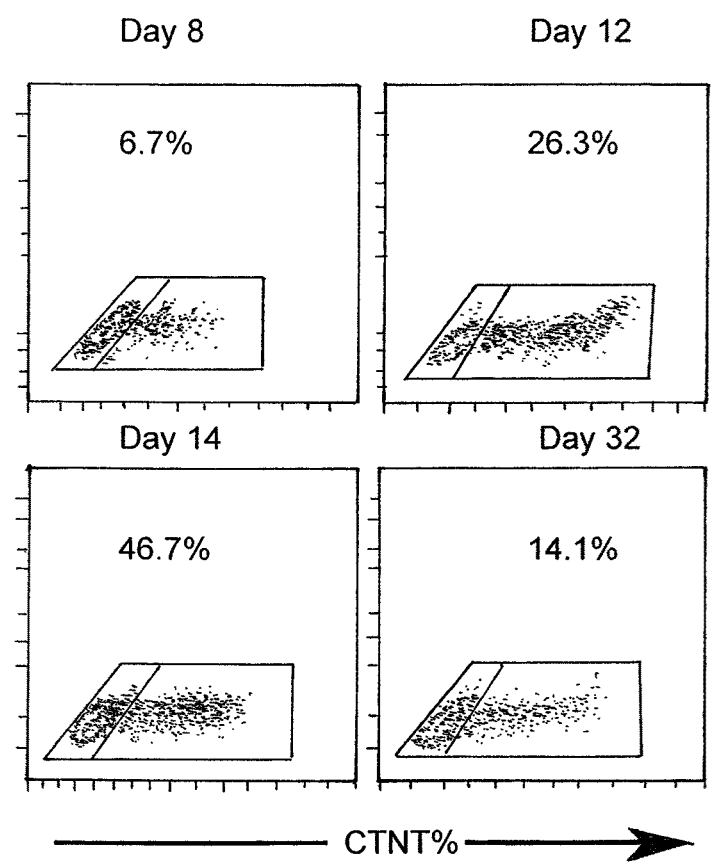
FIG. 21 shows the kinetics of the development of CTNT+ cells in EBs.
Figure 22:
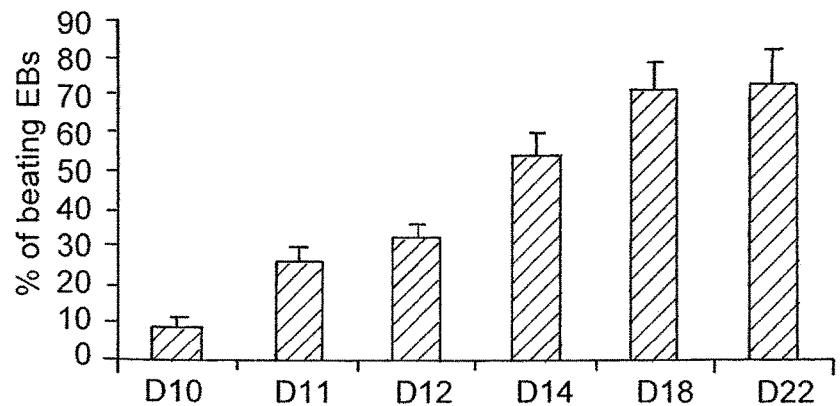
FIG. 22 shows the kinetics of the development of contracting EBs induced with the protocol in FIG. 1. Between 150-200 EBs were scored at each time point for the presence of contracting EBs. Bars represent standard error of the mean of three independent experiments.

To direct the differentiation of hESC to the cardiac lineage, a staged protocol was designed that involves the induction of a primitive streak-like population, the patterning of cardiac mesoderm and the specification of the cardiovascular lineages using combinations of BMP4, activin A, VEGF, bFGF and DKK1, factors known to play a role in mesoderm induction and cardiac specification in different model systems. An outline of the protocol is shown in FIG. 1. With the protocol exemplified here, hESC were first differentiated in the presence of BMP4 for 24 hours to allow the formation of EBs. The combination of activin and BMP4 at stage 1 induced a primitive streak-like population and mesoderm as demonstrated by the upregulation and transient expression of T (Brachyury) and WNT3a, genes known to be expressed in these populations in the mouse (FIG. 6). At stage 2, VEGF and the Wnt inhibitor DKK1 further patterned the mesoderm and promoted the expansion and maturation of KDR+ progenitor population. bFGF was added again at day 8 of differentiation to support the continued expansion of the developing cardiovascular lineages. This protocol supports cardiac development within the EBs as demonstrated by the emergence of contracting cells and cells that expressed cardiac troponin T (CTNT) (FIG. 2), α-actinin, a/β myosin heavy chain, ANP and connexin 43 (FIGS. 20, 21). The highest frequency of CTNT+ cells was routinely observed between days 14 and 16 of culture (FIGS. 2, 21) although this population could be maintained within the EBs over a two-month period. The kinetics of development of contracting EBs paralleled the emergence of the CTNT+ population (FIG. 22).

Example 3

Role of Wnt Signaling on Emergence of Cardiac Lineage from Human ES Cells

Figure 3:
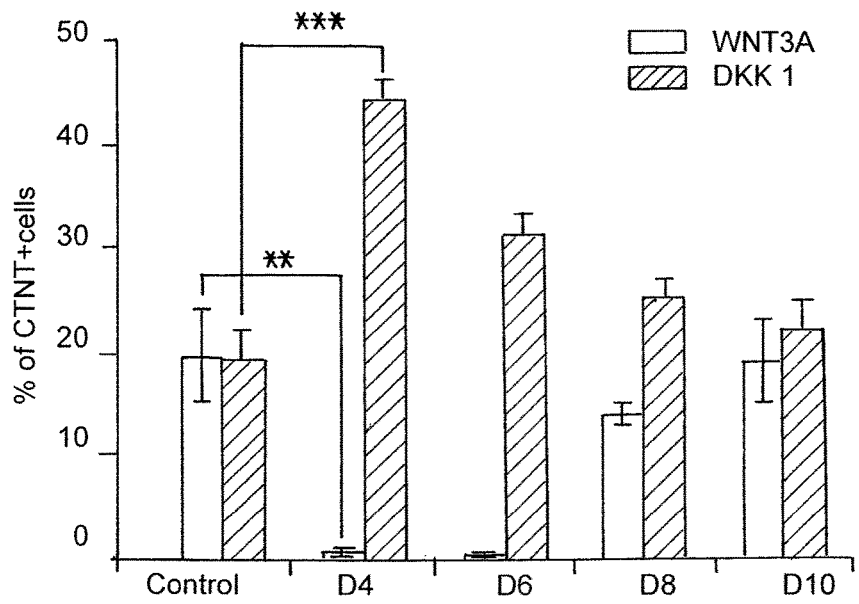
FIG. 3 shows the frequency of CTNT+ cells in day 14 EBs following manipulation of the Wnt signaling pathway at different stages.

The role of Wnt signaling pathway on emergence of the cardiac lineage from the human ES cells was investigated, specifically focusing on that stage beyond primitive streak induction (Stage2). EBs were induced in the presence of BMP4, bFGF and activin A as outlined in the protocol. Either Wnt3A or DKK1 were added to the cultures at the days indicated in FIG. 3. These factors were maintained in the cultures throughout the 14-day period. VEGF and bFGF were added at the indicated times. At day 14, the EBs were harvested and analyzed as above. The control was cultures that did not receive WNT or DKK1. Addition of DKK1 to the EBs at day 4 of differentiation led to a more than two-fold increase in the frequency of CTNT+ cells (up to 40%) at day 14 of culture (FIG. 3). The effect of DKK1 was less pronounced if added at day 6 or 8 and there was no enhancement of the frequency of CTNT+ cells if the addition was delayed to day 10 of differentiation. Wnt3A had the opposite effect and completely suppressed development of CTNT+ cells if added to the cultures at days 4 or 6. These findings indicate that stage-specific inhibition of the canonical Wnt pathway is necessary to promote cardiac specification of the BMP4/activin induced PS population.

Example 4

Role of BMP4, Activin A and bFGF in Induction of the Cardiac Lineage

Figure 5:
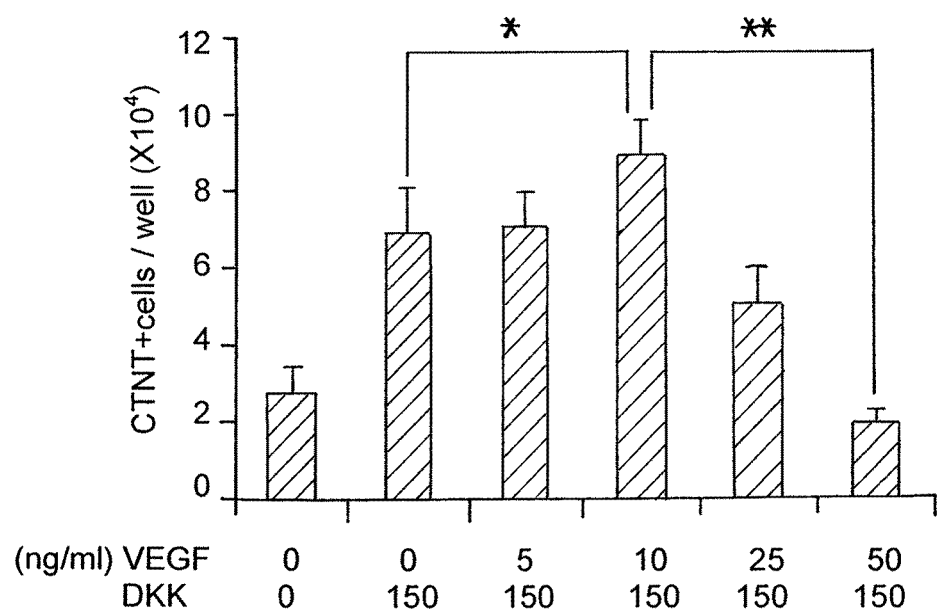
FIG. 5 shows the total number of CTNT+ cells per well of 24 well plates for day 14 EBs treated with the indicated combinations of VEGF and DKKI. For FIGS. 1-5, bars represent the standard error or the means of three independent experiments. Statistical analysis was performed with the unpaired t-test. *P=0.07, P<0.01, *P<0.001.
Figure 23:
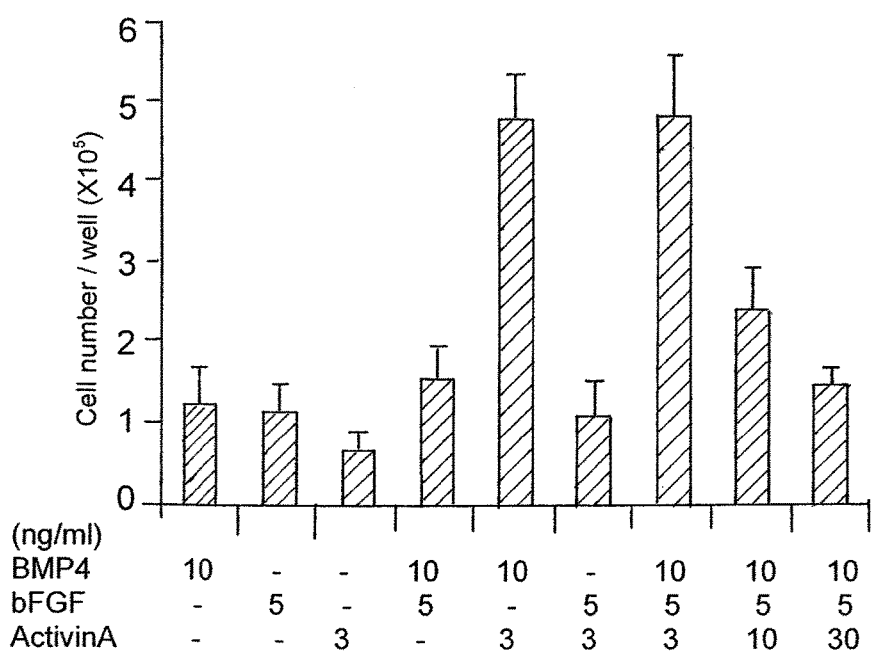
FIG. 23 shows the total number of cells per well of 24 well plates in day 14 EBs following induction with the combinations of factors indicated below the graph.
Figure 24:
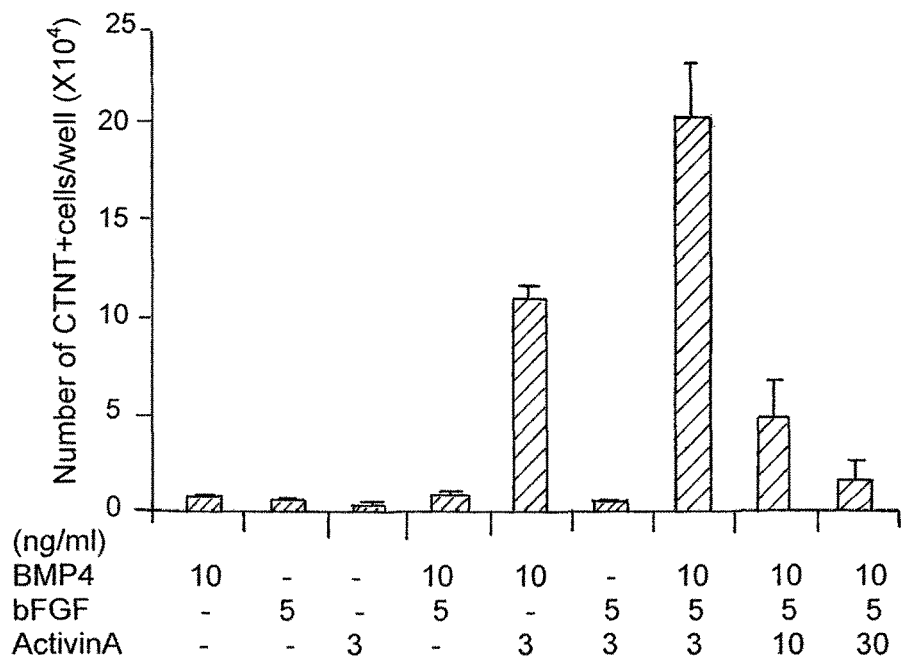
FIG. 24 shows the total number of CTNT+ cells per well of 24 well plates in day 14 EBs following induction with the combinations of factors indicated below the graph.
Figure 25:
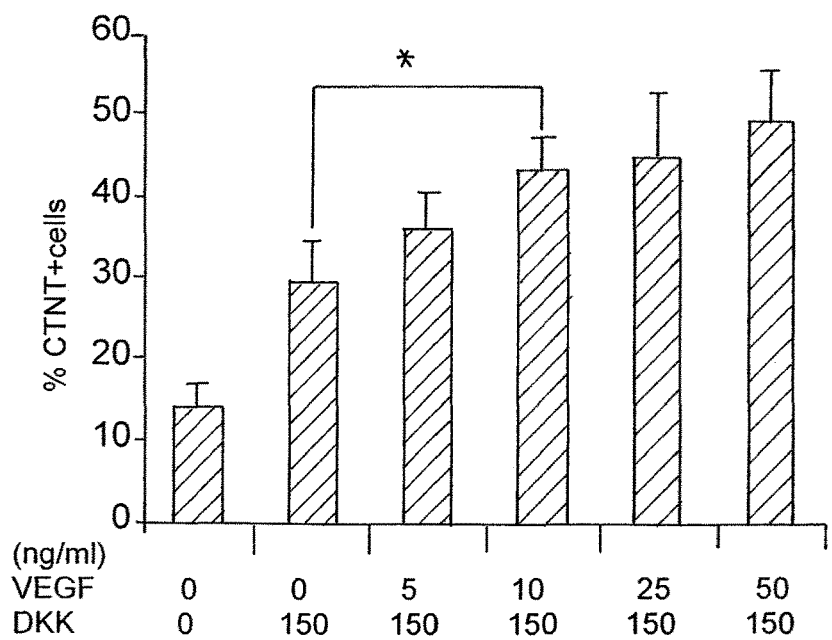
FIG. 25 shows the frequency of CTNT+ cells from day 14 EBs treated with the indicated combinations of VEGF and DKK.
Figure 26:
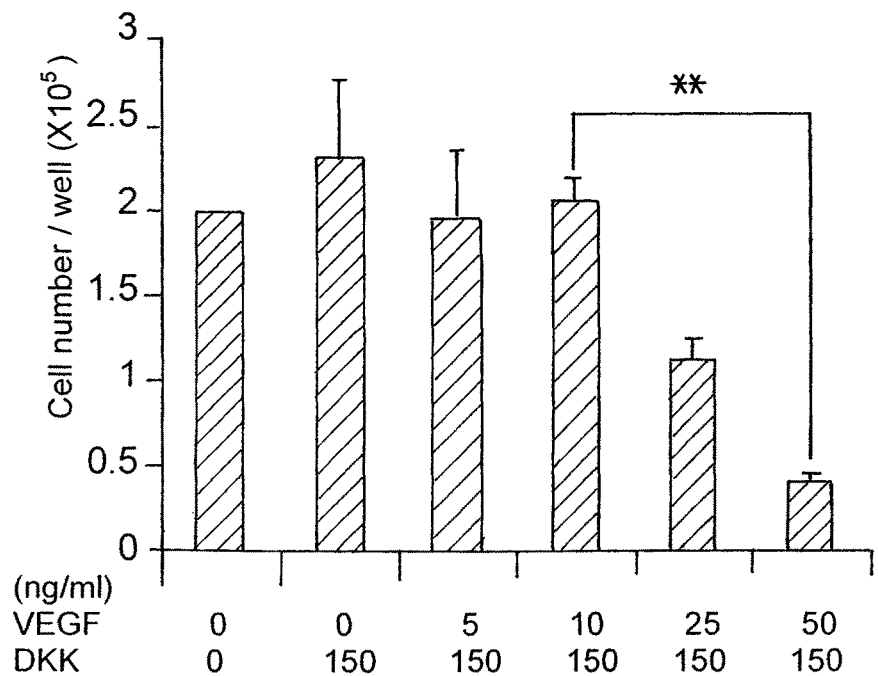
FIG. 26 shows the total number of CTNT+ cells per well of 24 well plates for day 14 EBs treated with the indicated combinations of VEGF and DKK. For FIGS. 23-26, bars represent standard error of the mean of three independent experiments. Statistical analysis was performed with unpaired t-text. *P<0.05, **P<0.01
Figure 27A:
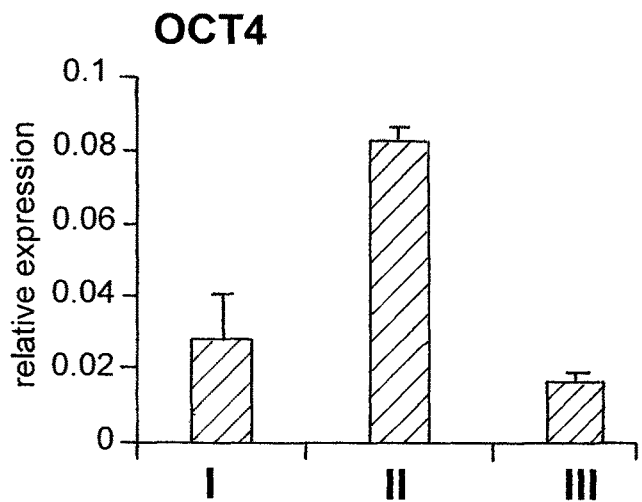
FIGS. 27a-g show quantitative RT-PCR analysis of three populations isolated from day 6 EBs. Average expression normalized to cyclophinin is shown. Bars represent standard error of the mean of three independent experiments.
Figure 27B:
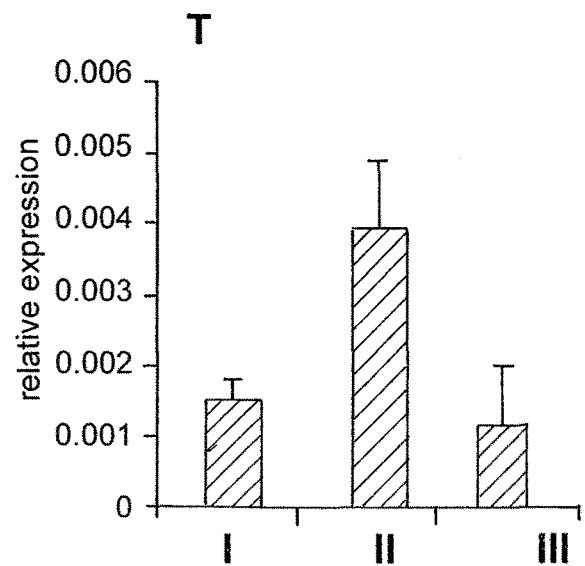
Figure 27C:
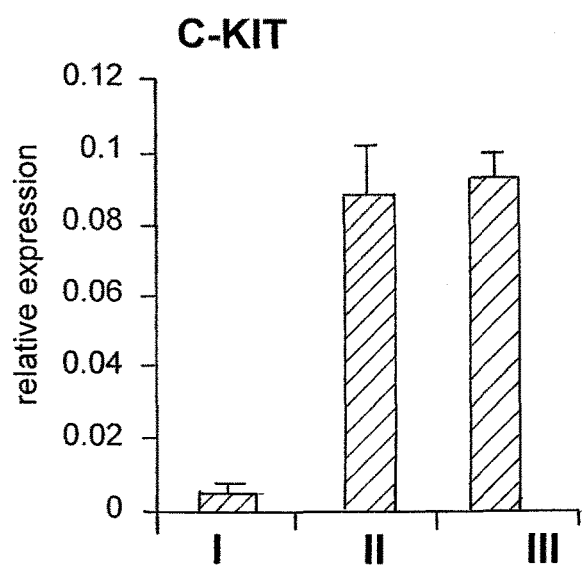
Figure 27D:
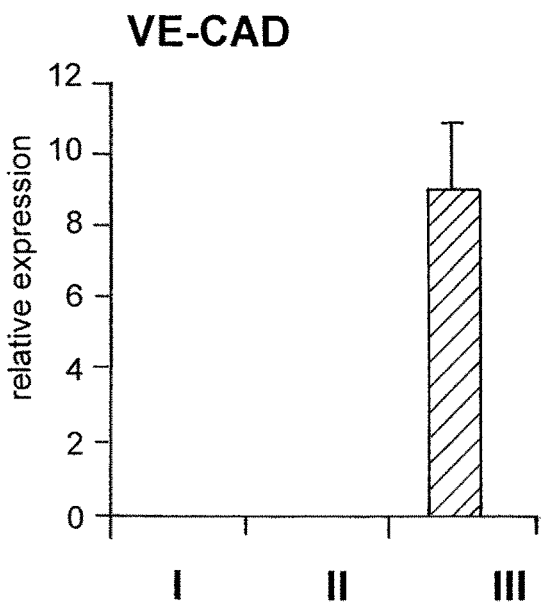
Figure 27E:
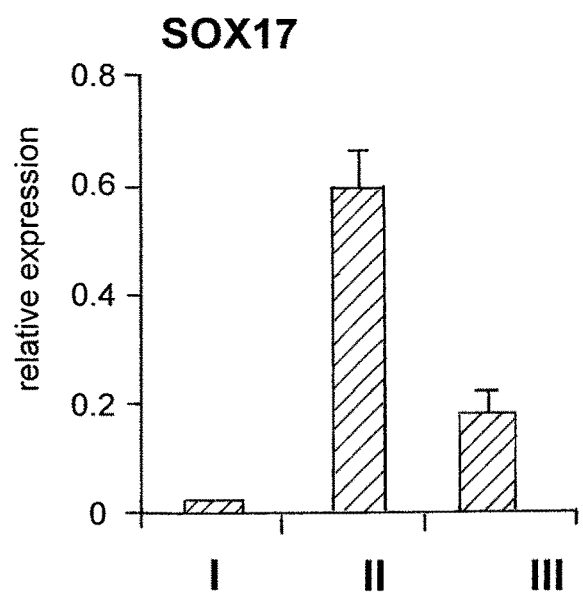
Figure 27F:
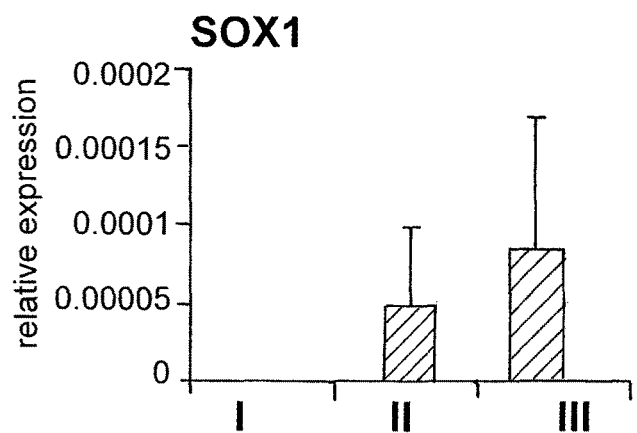
Figure 27G:
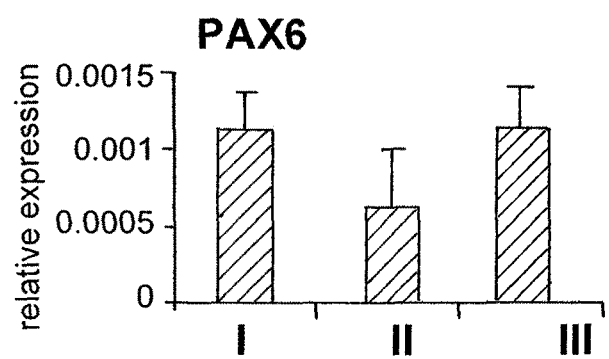

To evaluate the role of BMP4, activin A and bFGF in the induction of the cardiac lineage in hESC differentiation cultures, single factors as well as different combinations were tested during the induction stage (days 1-4). At day 4 the factors were removed and the EBs treated as outlined in FIG. 1. Day 4-14 EBs were treated with combinations of VEGF and DKK1 indicated in FIGS. 5, 25, and 26, with addition of bFGF after day 8. EBs were harvested at day 14 and analyzed for frequency of CTNT$^+$ cells for each combination and for total number of CTNT$^+$ cells per well of 24 well plates. BMP4, bFGF or activin A alone or the combinations of BMP4 and FGF or activin A and bFGF were poor inducers of cardiac development as demonstrated by the low frequency (FIG. 4) and total number of CTNT+ cells generated (FIGS. 23, 24). While BMP4 and activin A did induce significant numbers of CTNT+ cells, the combination of the 3 factors was the most potent and generated the highest frequency and total number of cardiac cells, routinely yielding cultures consisting of between 40% and 50% CTNT+ cells. While VEGF was not essential for cardiac development, the addition of 10 ng/ml of this factor did increase the total number of CTNT+ cells that developed. Increasing concentrations of VEGF above this concentration reduced the cell number in the cultures, resulting in a significant decrease in the total number of CTNT+ cells generated (FIGS. 5, 25 and 26).

Molecular analysis of the developing EBs revealed dynamic changes in expression patterns following the establishment of a primitive streak-like population. Together with T and WNT3A, expression of DKK1 was upregulated early and persisted through the 18-day time course (FIG. 6). Expression of endogenous DKK1, between days 2 and 4 of differentiation, may function to specify cardiac mesoderm, resulting in the establishment of the cardiac lineage in the absence of the addition of exogenous inhibitor (FIG. 3). KDR was expressed in undifferentiated ES cells. The levels of expression appeared to increase between days 4 and 6 and then persisted for the next 12 days. ISL1, a gene that marks progenitors of the secondary heart field in the early embryo, was expressed in the EBs between days 6 and 8, preceding the expression of the cardiac transcription factor Nkx2.5 that was first detected at day 8 of differentiation. Expression of two TBX transcription factors required for proper cardiac development TBX5, and TBX20, as well as the contractile proteins MLC2A and CTNT was upregulated between days 8 and 10 of differentiation, reflecting the onset of cardiac development.

Example 5

Figure 7:
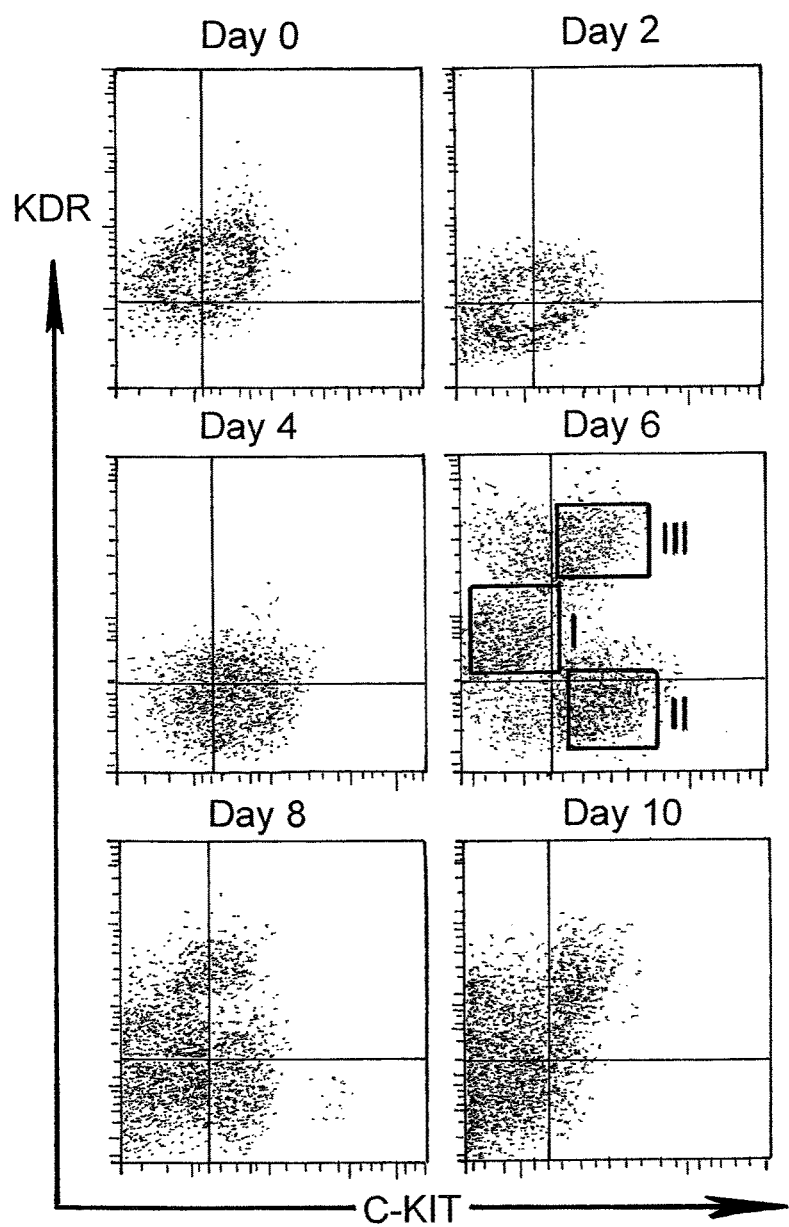
FIG. 7 shows flow cytometric analysis of different aged EBs.
Figure 8A:
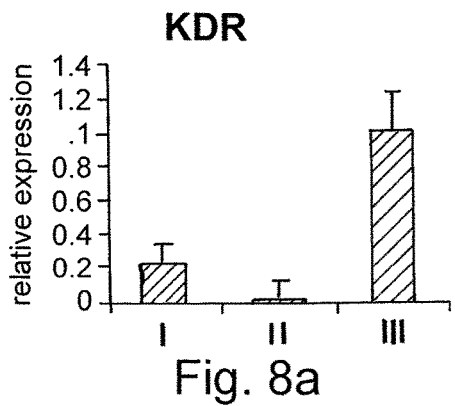
FIGS. 8a-h show quantitative RT-PCR gene analysis of the three populations isolated from day 6 EBs.
Figure 8B:
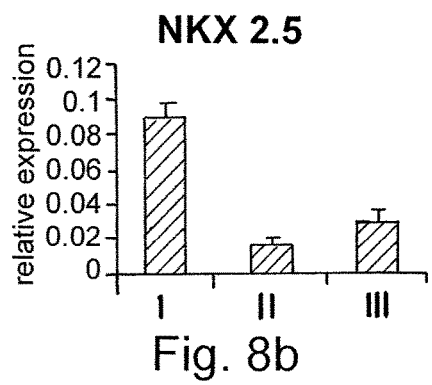
Figure 8C:
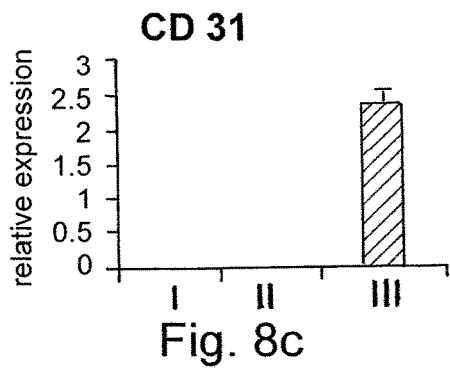
Figure 8D:
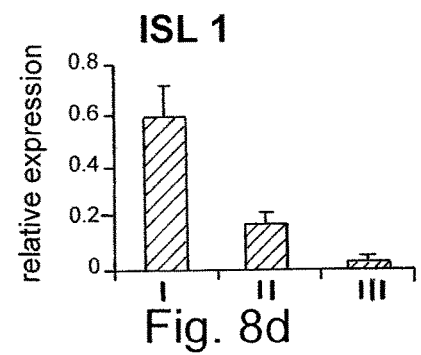
Figure 8E:
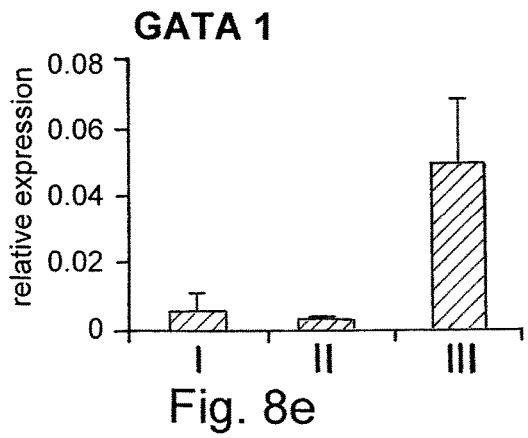
Figure 8F:
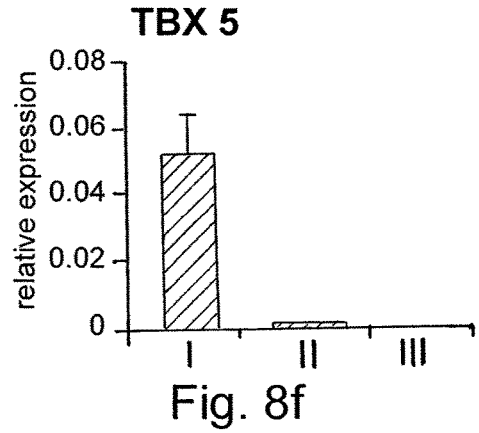
Figure 8G:
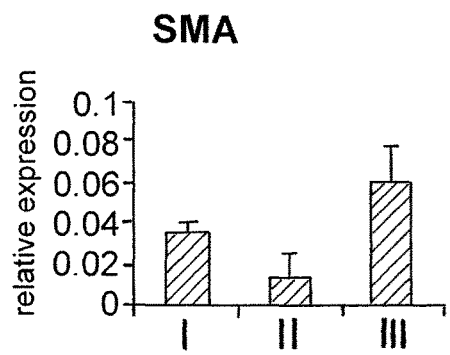
Figure 8H:
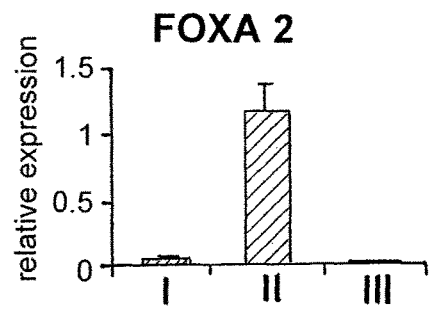

Identification of the $KDR^{low}/C\text{-}KIT^{neg}$ EB Population with Cardiovascular Potential Developing EBs were analyzed for expression of KDR and C-KIT. C-KIT was used as a potential marker to define distinct populations as its expression in mouse EBs identifies the earliest hemangioblast-derived hematopoietic and vascular progenitors as well as the anterior primitive streak and the developing endoderm. FIG. 7 shows flow cytometric analysis of different aged EBs. As shown in FIG. 7, three distinct populations, $KDR^{high}/C\text{-}K1T^+$, $KDR^{low}/C\text{-}KIT^{neg}$ and $KDR^{neg}/C\text{-}KIT^+$ can be resolved within the day 6 EBs. Development of the three populations was dependent on induction with both BMP4 and activin A (not shown). The three populations were isolated by cell sorting and analyzed for gene expression patterns and cardiac potential. FIG. 8 shows quantitative RT-PCR gene expression analysis of the three populations isolated from day 6 EBs. Average expression was normalized to cyclophinin. The $KDR^{high}/C\text{-}KIT^+$ population expressed CD3I, VE-CADHERIN and SMA, genes associated with vascular development, as well as GATA-I, a gene indicative of hematopoietic commitment (FIGS. 8, 27). Genes involved in cardiac development, including NKX2.5, ISL1 and TBX5 were expressed at highest levels in the $KDR^{low}/C\text{-}KIT^{neg}$ fraction. This fraction also expressed SMA, very low levels of GATA-1, but no detectable VE-CADHERIN or CD31. As SMA is expressed early in the cardiac lineage as well as in the VSM lineage, this expression could reflect the onset of cardiac development. The $KDR^{neg}/C\text{-}KIT^+$ cells expressed the highest levels of OCT4 and T of the 3 fractions, indicating the presence of residual undifferentiated ES cells as well as primitive streak-like cells. The relatively high levels of FOXA2 and SOX17 in this fraction suggest that it also contains cells undergoing commitment to the endoderm lineage. SOX1 and PAX6 were only detected at very low levels, suggesting little, if any, differentiation to the neuroectoderm lineage in the EBs at this stage of development (FIG. 27). Taken together, these expression patterns demonstrate that the $KDR^{high}/C\text{-}KIT^+$ population contains hematopoietic and vascular progenitors, the $KDR^{low}/C\text{-}KIT^{neg}$ population contains cardiac progenitors and the $KDR^{neg}/C\text{-}KIT^+$ population consists of a mixture of undifferentiated ES cells, primitive streak cells and endodermal cells.

Figure 9:
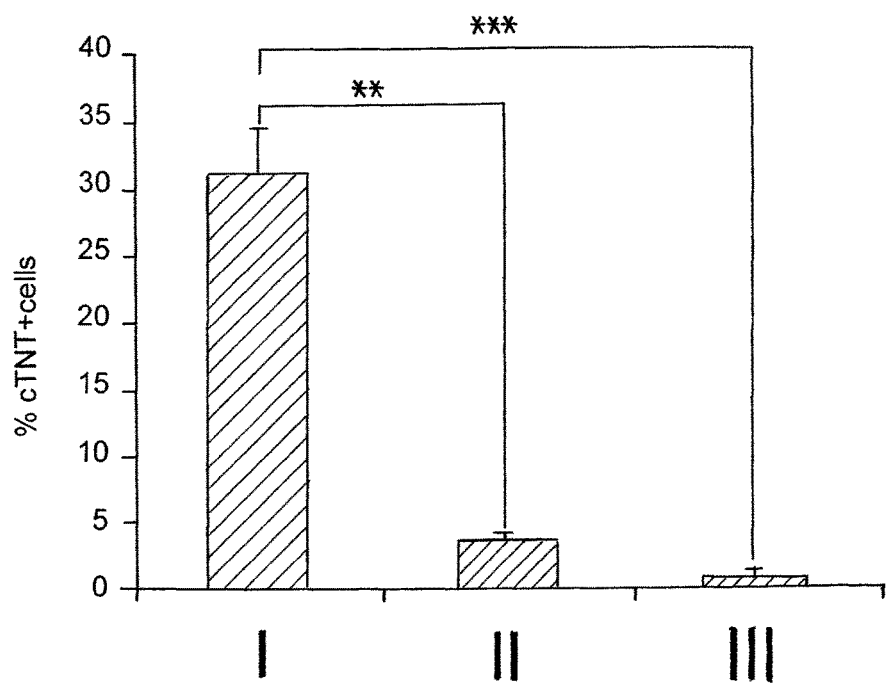
FIG. 9 shows cardiac potential of the three day 6 populations.
Figure 10:
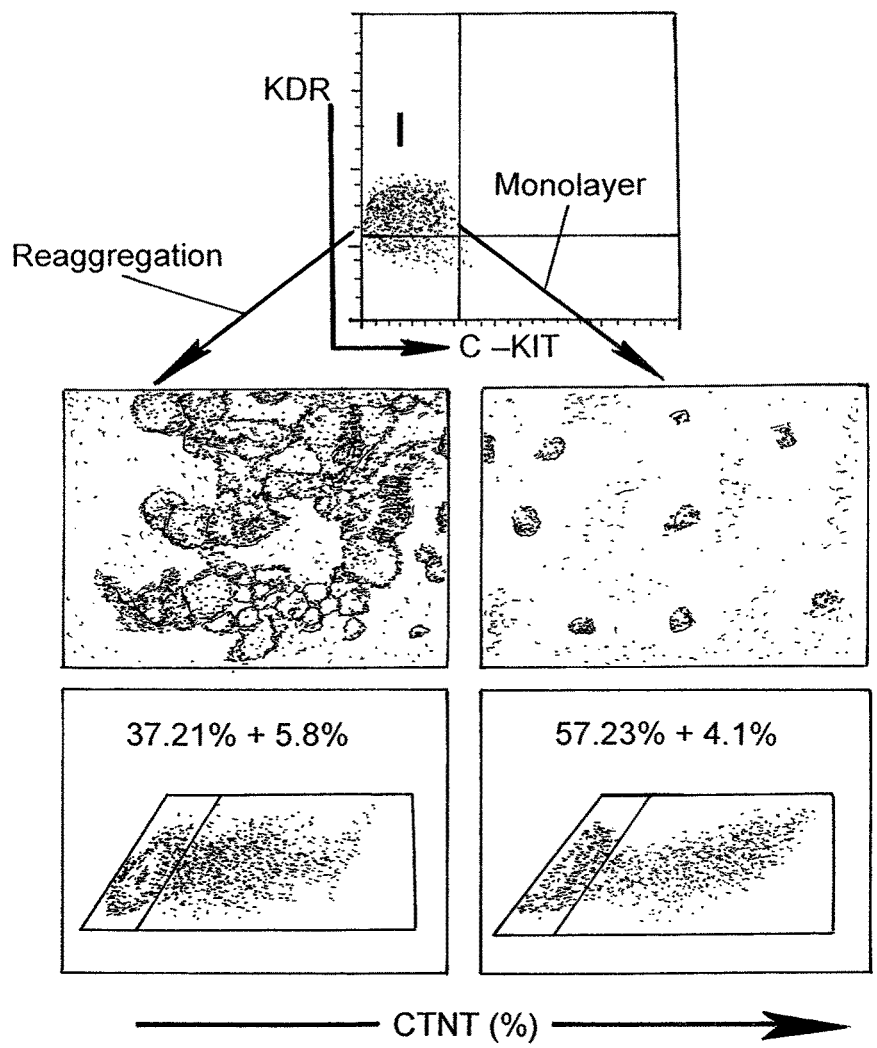
FIG. 10 shows the cardiac potential of the day 6 $KDR^{low}$/$C\text{-}KIT^{neg}$ population.
Figure 11A:
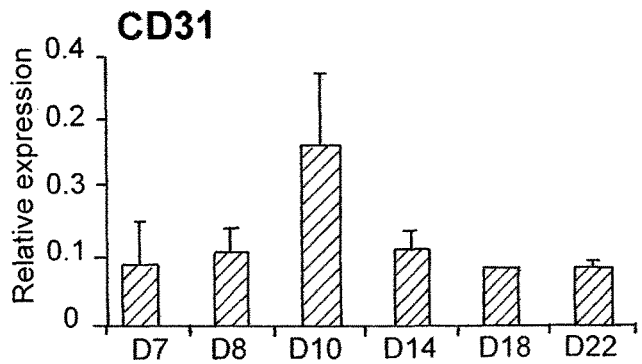
FIGS. 11a-j show quantitative RT-PCR expression analysis of adherent populations generated from the day 6 EB-derived $KDR^{low}$/$C\text{-}KIT^{neg}$ fraction.
Figure 11B:
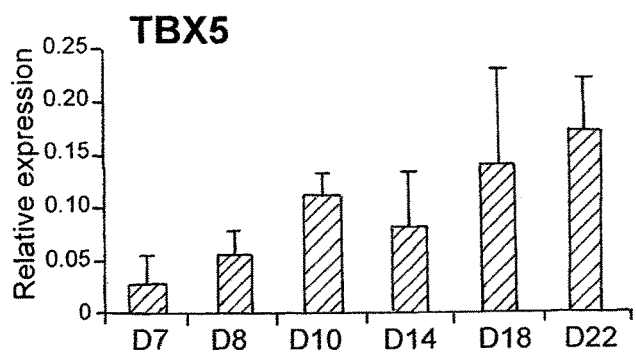
Figure 11C:
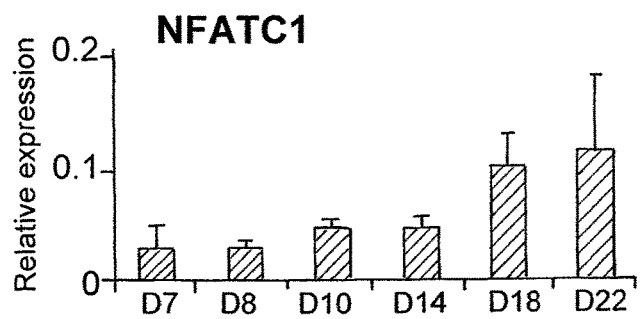
Figure 11D:
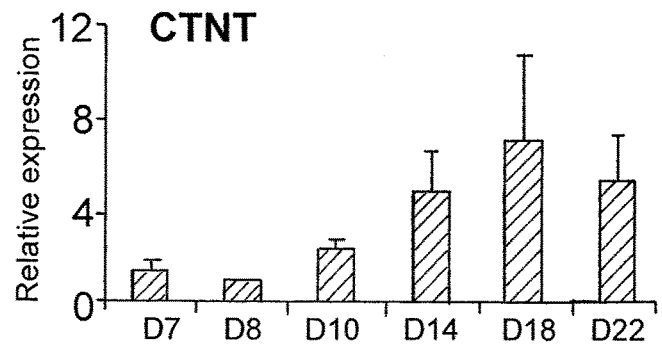
Figure 11E:
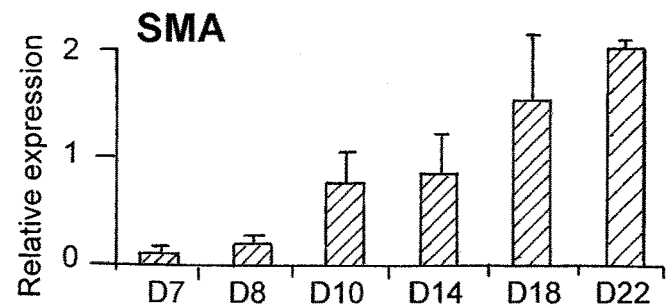
Figure 11F:
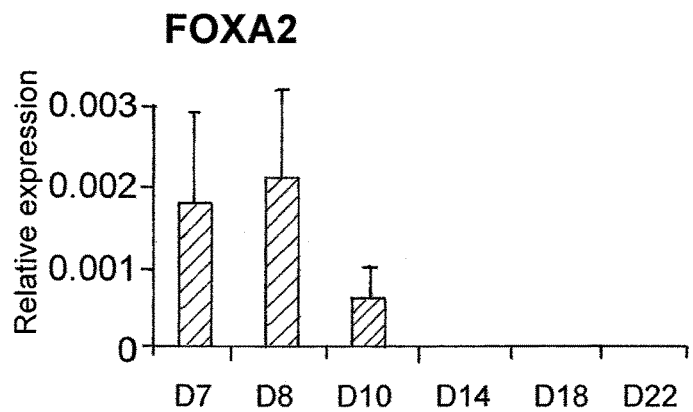
Figure 11G:
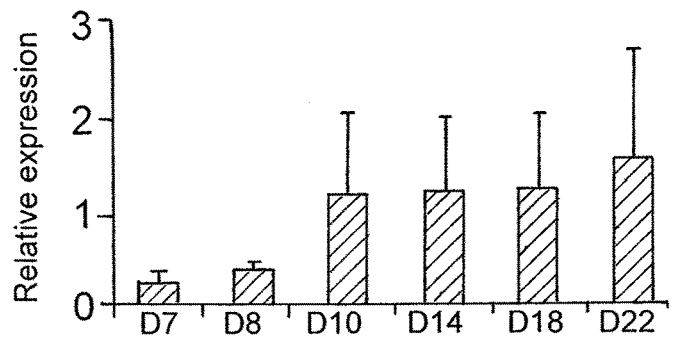
Figure 11H:
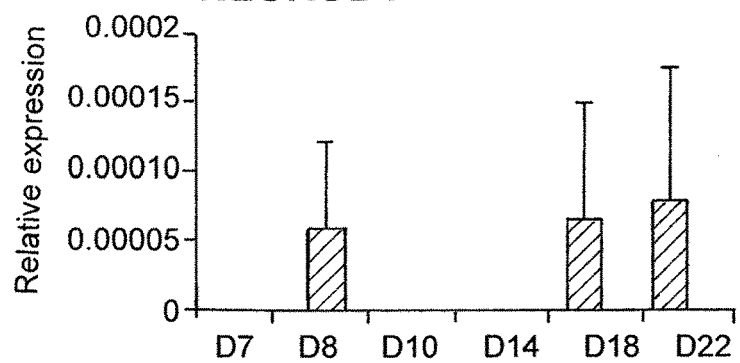
Figure 11I:
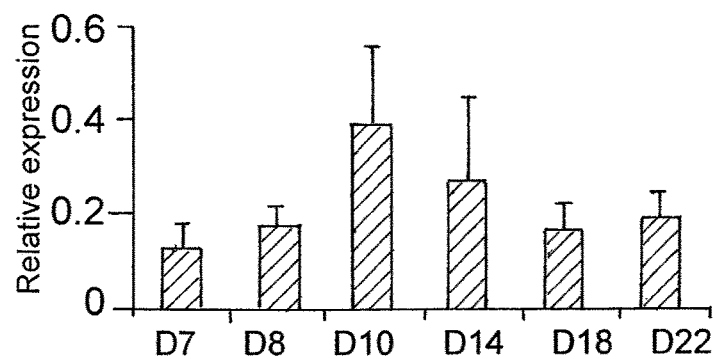
Figure 11J:
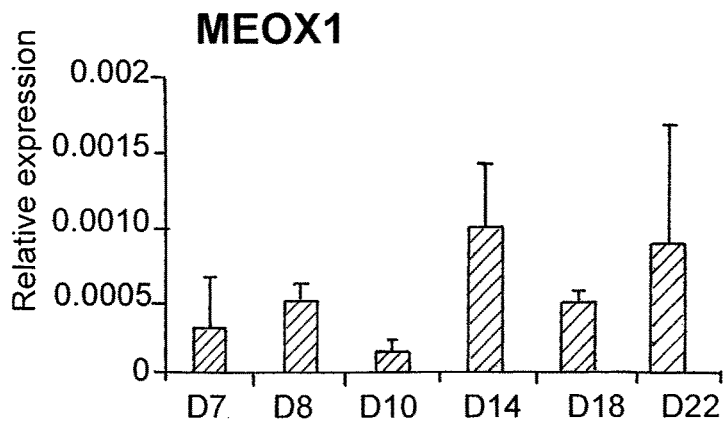
Figure 28:
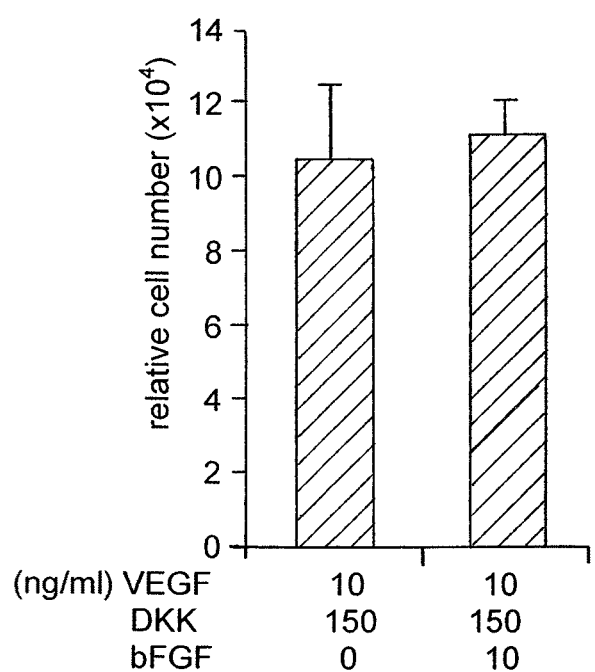
FIG. 28 is a graph of relative cell numbers after 10-14 days in monolayer culture of $KDR^{low}$/$C\text{-}KIT^{neg}$ populations isolated from day 6 EBs. 40,000 cells per well of 96 well plates were induced with the combinations of factors shown below the graph. Bars represent standard error of the mean of three independent experiments.
Figure 29:
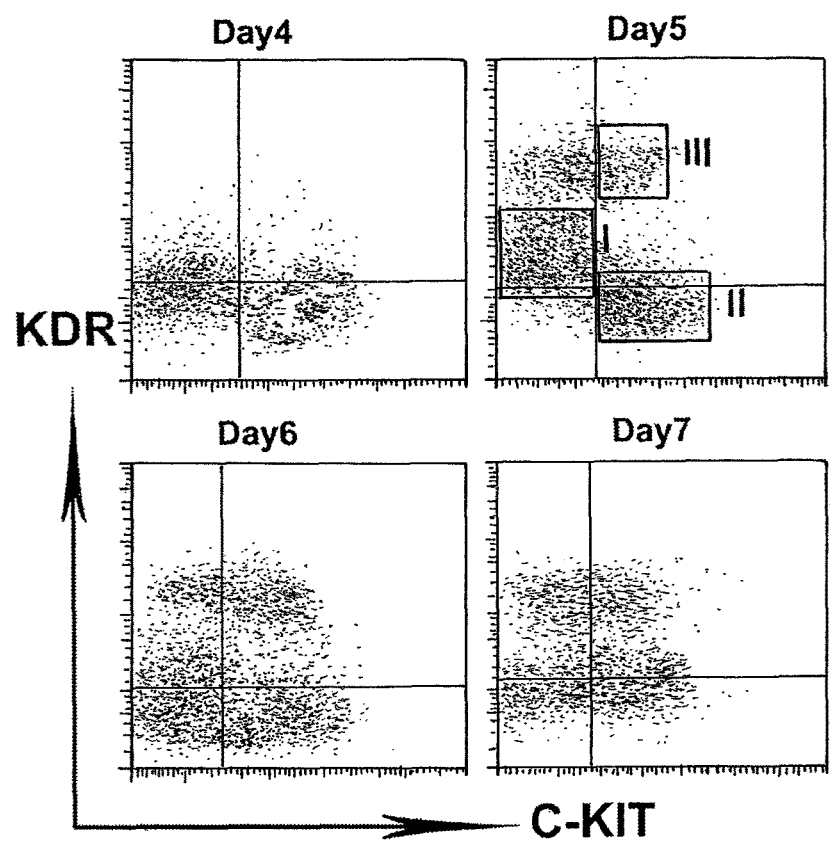
FIG. 29 shows flow cytometric analysis demonstrating the emergence of the three different KDR/C-KIT populations in EBs generated from H1 hESC.
Figure 30:
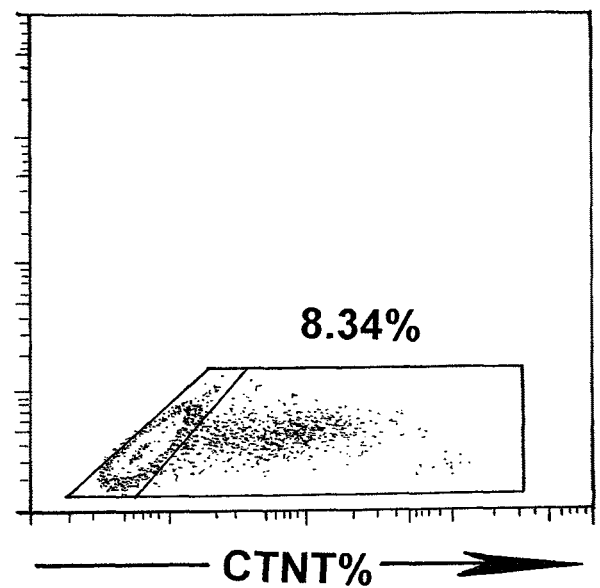
FIG. 30 shows the development of CTNT+ cells from the H1 hESC-derived $KDR^{low}$/$C\text{-}KIT^{neg}$ fraction following 7 days of culture.
Figure 31A:
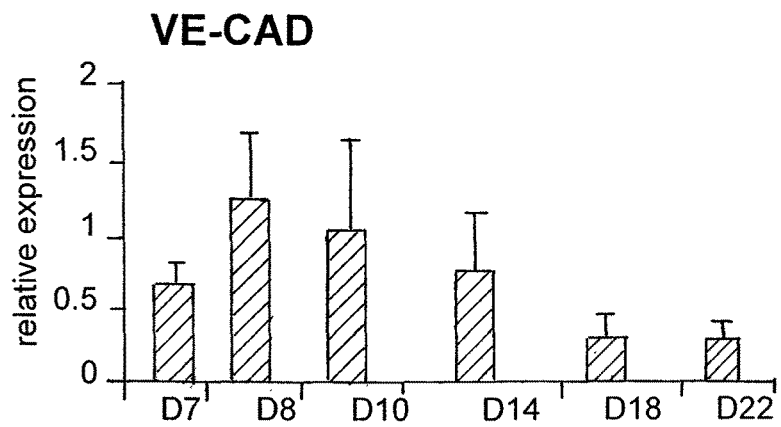
FIGS. 31a-i show quantitative RT-PCR expression analysis of $KDR^{low}$/$C\text{-}KIT^{neg}$-derived adherent populations cultured in the presence of VEGF (10 ng/mL), DKK1 (150 ng/mL) and bFGF (10 ng/mL). Cultures were harvested at the specified times and analyzed for the expression of the indicated genes. Average expression normalized to cyclophinin is shown.
Figure 31B:
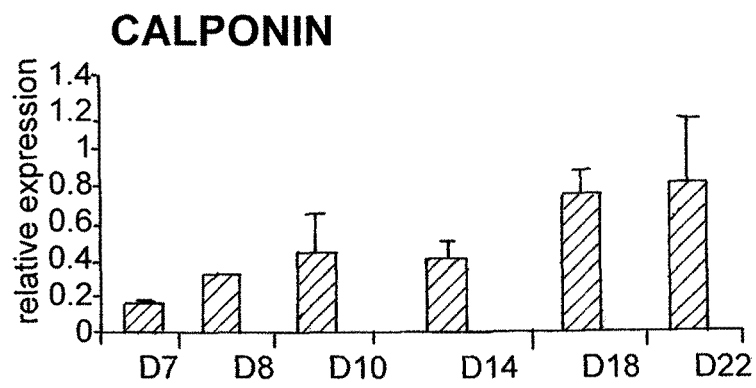
Figure 31C:
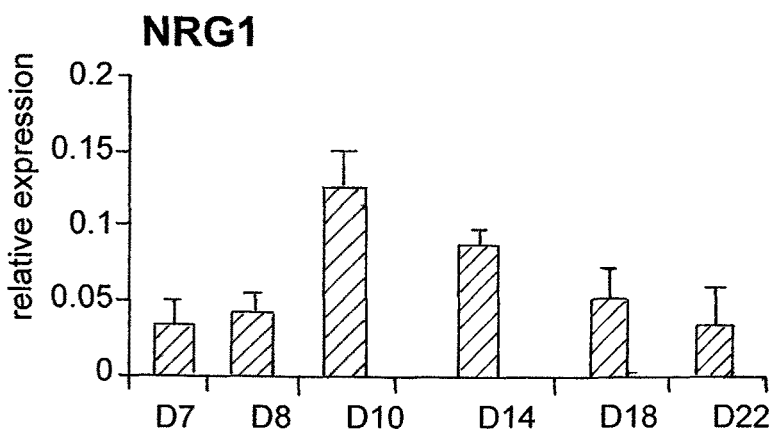
Figure 31D:
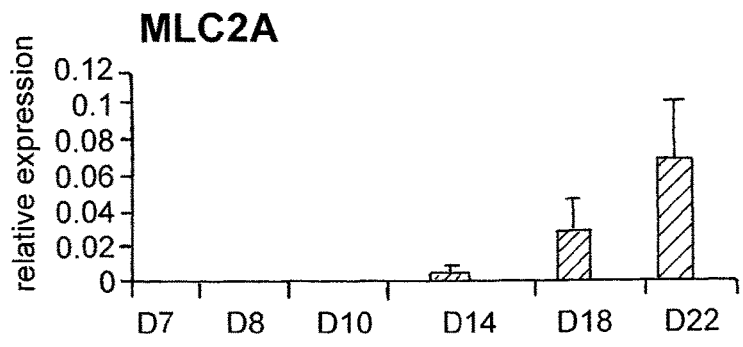
Figure 31E:
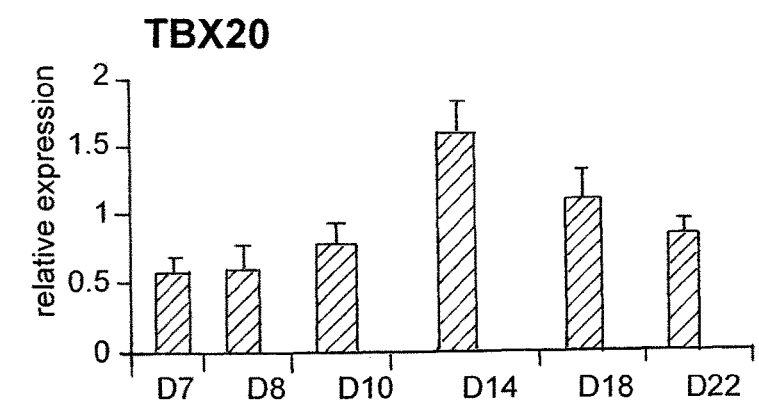
Figure 31F:
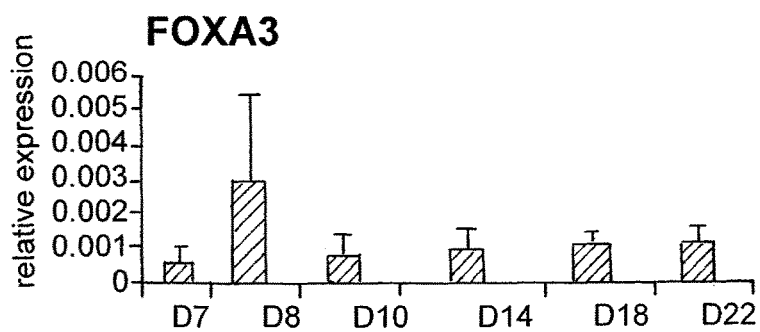
Figure 31G:
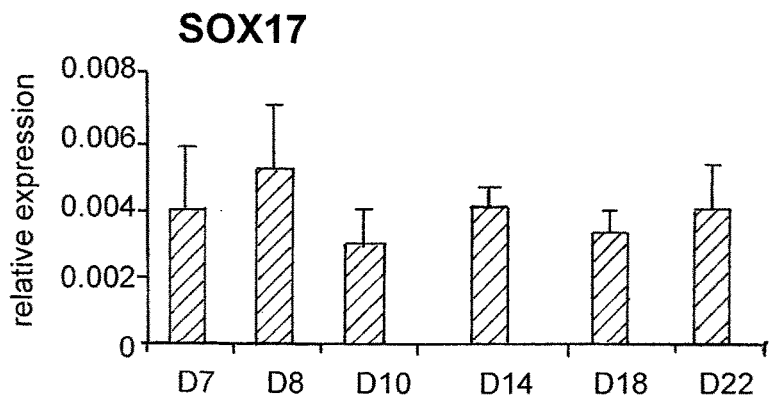
Figure 31H:
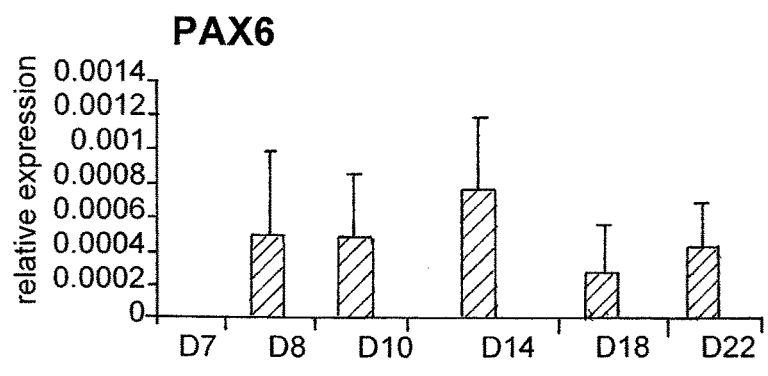
Figure 31I:
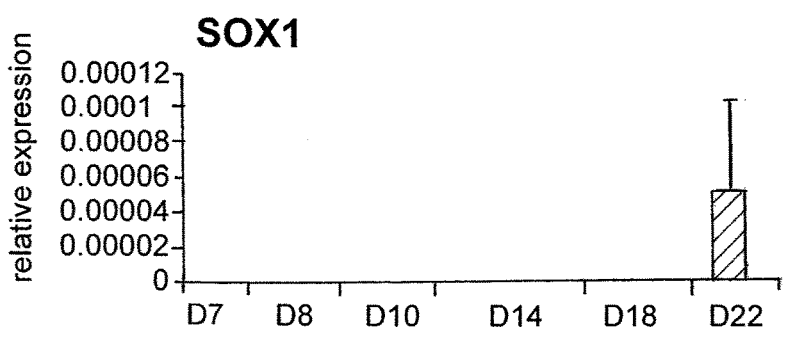

To monitor cardiac potential, the cells were plated either as monolayers on gelatin coated wells or allowed to reaggregate in low cluster dishes and cultured as aggregates. Specifically, cells were isolated from day 6 EBs and cultured on gelatin-coated wells as monolayers with VEGF (10 ng/ml), DKK1 (150 ng/ml) and bFGF (10 ng/ml). $CTNT^+$ cells were analyzed after 10 days culture. Results are shown in FIG. 9. $KDR^{low}/C\text{-}KIT^{neg}$ cells from day 6 EBs were sorted and cultured as a monolayer or as aggregates in low cluster wells with VEGF (10 ng/ml) and DKK1 (150 ng/ml). Cultures were harvested and analyzed for the presence of $CTNT^+$ cells following 7-10 days of differentiation. Results are shown in FIG. 10. The numbers (%) represent the mean+/− standard error of three independent experiments. Bars represent standard error of the mean of three independent experiments. Statistic analysis was performed with unpaired t-test. *$P<0.01$, ***$P<0.001$. The $KDR^{low}/C\text{-}KIT^{neg}$ population displayed the greatest cardiomyocyte potential (FIG. 9) and readily generated CTNT+ cells and populations of contracting cells in both the aggregates in suspension cultures as well as in the adherent monolayers (FIG. 10). Approximately 40% of the cells within the aggregates were CTNT+ whereas greater than 50% of the monolayer cultures consistently expressed this marker. The high frequency of cardiomyocytes in the monolayer cultures routinely led to the development of sheets of cells contracting as a synchronous mass. The isolated $KDR^{low}/C\text{-}KIT^{neg}$ cells expanded approximately 1.5-fold as aggregates (data not shown) and 3-fold in the monolayer cultures (FIG. 28). With the induction protocol and sorting strategy outlined, an output of 1 cardiomyocyte per 4 input hESC was estimated. In a typical experiment, $2\times10^6$ hESC generated $1\times10^6$ day 6 EB cells of which 30% ($3.0\times905$ cells) represented the $KDR^{low}/C\text{-}KIT^{neg}$ fraction. This population expanded 3-fold ($1\times10^6$ cells) in the monolayer culture format to yield a population that consisted of approximately 50% cardiomyocytes ($5\times10^5$). Kinetic analysis of EBs generated from a second hESC line, H1 demonstrated the development of the 3 KDR/C-KIT populations at day 5 rather that day 6 of differentiation. Analysis of the day 5 $KDR^{low}/C\text{-}KIT^{neg}$ population indicated that it also displayed cardiac potential (FIGS. 29, 30).

Example 6

Characterization of $KDR^{low}/C\text{-}KIT^{neg}$-Derived Lineages

Quantitative RT-PCR expression analysis of adherent populations generated from the day 6 EB-derived $KDR^{low}/C\text{-}KIT^{neg}$ fraction plated with VEGF (10 ng/ml), DKK1 (150 ng/ml) and bFGF (10 ng/ml) was performed. Cultures were harvested at the indicated days in FIG. 11 and the cells were analyzed for expression (D7 represents populations one day following plating). Average expression normalized to CYCLOPHININ is shown. Bars represent standard error of the mean of three independent experiments.

Expression analysis (qPCR) of $KDR^{low}/C\text{-}KIT^{neg}$-derived adherent populations at different days following plating demonstrated the upregulation of genes associated with endothelial (CD31, VE-CADHERIA), VSM (CALPONIN, SMA), cardiac development (NKX2.5, ISL1, TBX5, TBX20) and cardiac maturation (CTNT, MLC2A) (FIGS. 11, 31). Expression of NFATC and Neuregulin 1 (NRG1) suggest the presence of endocardium in the cultures. The low levels of NEUD, PAX6, SOX1, FOXA2, FOXA3, SOX17 and MEOX1 expression indicate that the cultures are not contaminated with neuroectoderm, endoderm or somatic mesoderm (FIGS. 11, 31).

$KDR^{low}/C\text{-}KIT^{neg}$ cells were isolated from day 6 EBs and cultured as a monolayer with the different combinations of factors indicated below the graph in FIG. 12. Cells were harvested and analyzed for the presence of CTNT+, CD31+ and SMA+ cells following 10-12 days culture. SMA antibody can stain both cardiomyocytes and smooth muscle cells. The number (%) represent standard error of the mean of three independent experiments.

Figure 12:
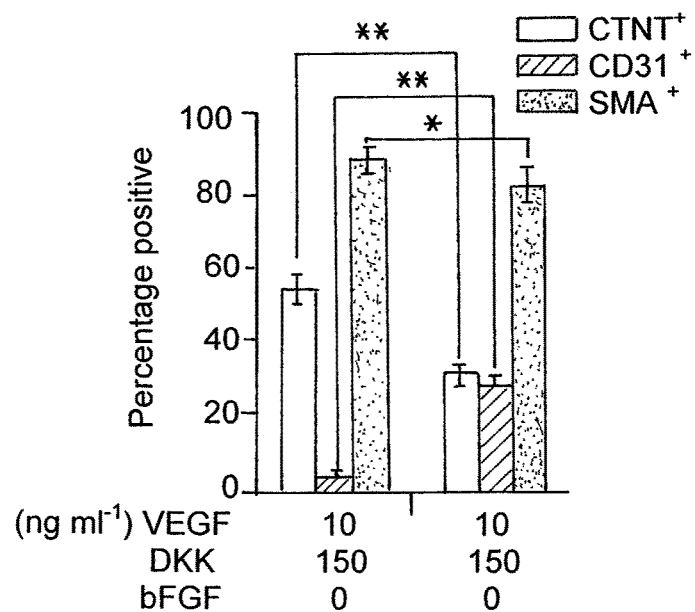
FIG. 12 shows an analysis for the presence of CTNT+, CD31+ and SMA+ cells following 10-12 days of culture of the $KDR^{low}$/$C\text{-}KIT^{neg}$ population.

Flow cytometric analysis of $KDR^{low}/C\text{-}KIT^{neg}$-derived adherent cells cultured for 10-12 days in VEGF and DKK1 revealed that almost 90% expressed SMA, 50% expressed CTNT and 4% expressed CD31 (FIG. 12). Addition of bFGF to the cultures reduced the proportion of CTNT+ cells to 30% and increased the CD31+ population to 30%. The proportion of SMA+ cells decreased modestly to an average of 80% in the presence of bFGF. The addition of bFGF did not significantly influence the cell number in the monolayer cultures (FIG. 28). These findings clearly indicate that the majority of cells within $KDR^{low}/C\text{-}KIT^{neg}$-derived population are of the cardiovascular lineages. They also show that bFGF can influence the proportion of cardiomyocytes and endothelial cells that develop in this population.

Immunostaining analysis of the $KDR^{low}/C\text{-}KIT^{neg}$-derived population cultured in VEGF, DKK1 and bFGF demonstrated the presence of CD31+, VE-Cadherin+ and von Willebrand Factor+ endothelial cells, of CTNT+ cardiomyocytes and of SMA+, SMHC+ and Caldesmon+ cells indicative of VSM development. The immature cardiomyocytes within the population expressed both CTNT and SMA, whereas the VSM cells expressed only SMA. To further characterize the $KDR^{low}/C\text{-}KIT^{neg}$-derived endothelial cells, the population was expanded in the presence of VEGF and bFGF and then cultured on Matrigel-coated cover slips. Under these conditions the cells formed a lattice indicative of endothelial cell organization into tube-like structures. The cells within these structures expressed CD31 and displayed the capacity to take up Dil-AC-LDL confirming their endothelial phenotype. The findings from the immunostaining analysis are consistent with those from the flow cytometric studies and demonstrate that the $KDR^{low}/C\text{-}K1T^{neg}$-derived population consists of cells of the cardiac, endothelial and vascular smooth muscle lineages.

$KDR^{low}/C\text{-}K1T^{neg}$-derived cells were also transplanted into the hearts of NOD/SCID mice to document their developmental potential in vivo. A GFP expressing version of the hES2 cell line was used for these studies. Histological analyses revealed the presence of GFP+ cells in the hearts following transplantation. Detection of GFP with an antibody identified the same population as visualized by epifluorescence, indicating that the GFP signal represents the presence of donor cells and does not result from background fluorescence. GFP+ populations co-expressing either α-actinin, CD31 or SMHC were detected in the grafts, indicating differentiation to the cardiac, endothelial and vascular smooth muscle lineages in vivo. Teratomas were not detected in any of the transplanted animals (N>10). To further evaluate the in vivo potential of this population, $KDR^{low}/C\text{-}KIT^{neg}$-derived cells were transplanted directly into infarcted hearts of SCID beige mice. When analyzed 2 weeks later, animals transplanted with the $KDR^{low}/C\text{-}KIT^{neg}$-derived cardiovascular population had a 31% higher ejection fraction than those injected with media alone (56%+/−3.6% vs 39%+/−4.8%, p=0.008). These findings are consistent with previous reports and demonstrate that transplantation of hESC-derived cardiomyocytes leads to improvement in cardiac function in rodent models of myocardial infarction.

Example 7

Identification and Characterization of Cardiovascular Colony-Forming Cells

Figure 13:
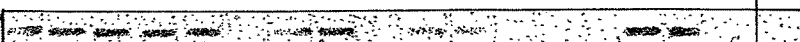
FIG. 13 depicts an expression analysis of 4-day-old cardiovascular colonies isolated from mixed RFP/GFP cultures.
Figure 32:
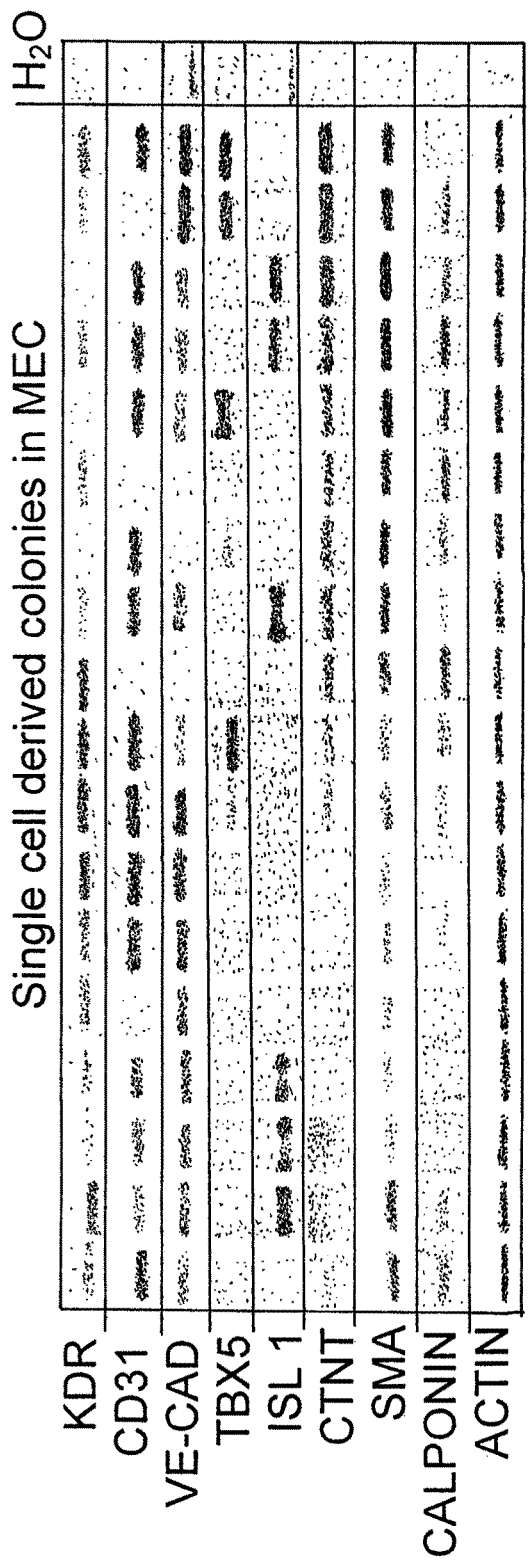
FIG. 32 shows expression analysis of individual 4-day-old cardiovascular colonies generated from the hES2-derived $KDR^{low}$/$C\text{-}KIT^{neg}$ population.

When plated in methylcellulose in the presence of VEGF, bFGF and DKK1, $KDR^{low}/C\text{-}KIT^{neg}$-derived cells generated small compact colonies within 4 days of culture. PCR analysis of individual 4-day-old colonies demonstrated co-expression of markers indicative of cardiac (CTNT), vascular (CD31 and/or VE-CADHERIN) and VSM (SMA and/or CALPONIN) development (FIGS. 13, 32). When maintained in culture for a further 6 days, a portion of these colonies generated contracting cells, confirming that they contain cardiomyocytes. ISL1 and TBX5 were typically not expressed in the same colonies, suggesting that their expression may define colonies that contain distinct subpopulations of developing cardiac cells from different heart fields. Immunostaining of adherent populations from individual colonies grown on cover slips revealed the presence of SMA+, CTNT+ and VE-CAD+ cells, confirming that these colonies do have cardiac, endothelial and VSM potentials.

Figure 14:
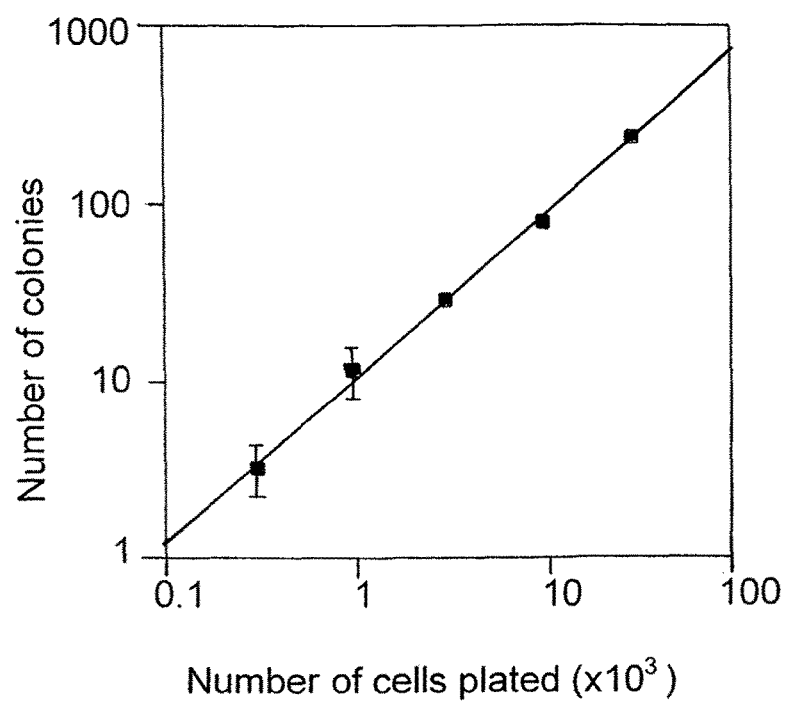
FIG. 14 depicts a cell dose response showing the relationship between the number of $KDR^{low}$/$C\text{-}KIT^{neg}$-derived cells plated and the number of cardiovascular colonies that develop.

Two different approaches were used to determine if the cardiovascular colonies are clonal. First, $KDR^{low}/C\text{-}KIT^{neg}$-derived cells from GFP expressing hESC were mixed in the methylcellulose assay with $KDR^{low}/C\text{-}KIT^{neg}$-derived cells from hESC engineered to express red fluorescent protein (RFP) in the methycellulose colony assay. Colonies analyzed 4 days later were found to express either GFP or RFP but not both (FIG. 13), a finding consistent with the interpretation that they arise from a single cell and do not form as a result of cell aggregation. As a second approach, a cell dose response experiment was performed, in which different numbers of $KDR^{low}/C\text{-}KIT^{neg}$-derived cells were plated in the cardiac methylcellulose cultures. The relationship between the number of colonies that develop and the number of cells plated was linear, with a slope approaching one, further supporting the notion that the colonies are derived from a single cell (FIG. 14). Taken together, these findings indicate that these colonies represent clones of cardiovascular cells derived from a cardiovascular colony-forming cell (hCV-CFC).

Figure 15:
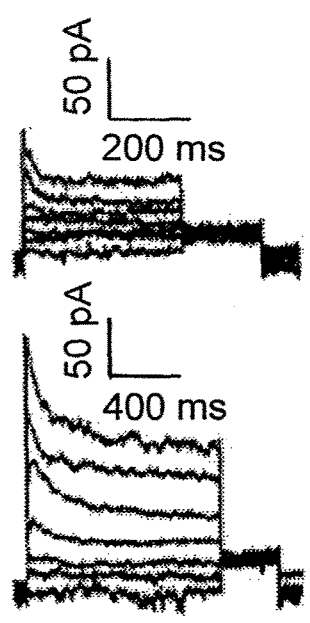
FIG. 15 depicts exemplar traces showing whole-cell voltage clamp recordings of transient outward K+ current ($I_{to}$) natively expressed in $KDR^{low}$/$C\text{-}KIT^{neg}$-derived cardiomyocytes.
Figure 16:
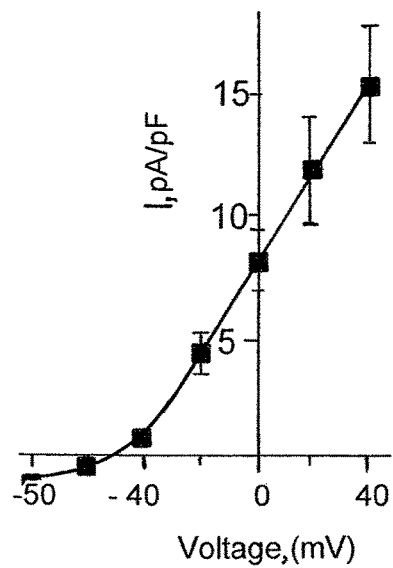
FIG. 16 shows mean current density-voltage relationship for cells as in FIG. 15. From a batch of 10 cells, 8 showed the $I_{to}$ current and the mean+/−SEM current densities were plotted using traces from these 8 cells.
Figure 17:
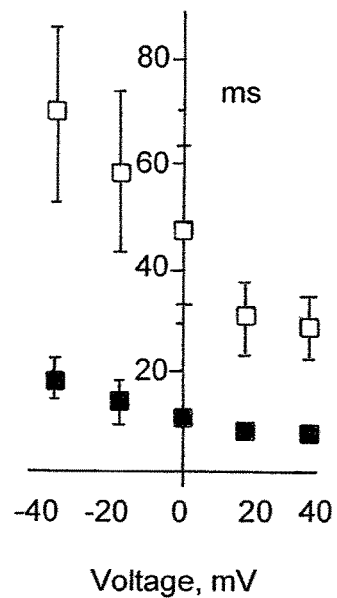
FIG. 17 shows mean time-to-peak current (solid squares) and inactivation τ (open squares) for cells as in FIG. 16 (n=8).
Figure 18:
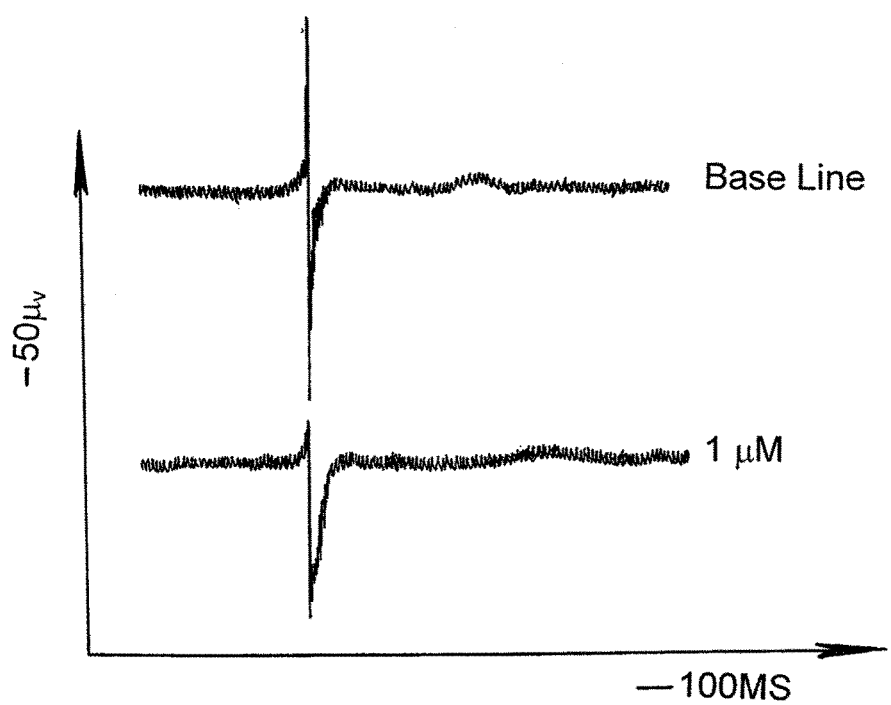
FIG. 18 shows electrical activity for $KDR^{low}$/$C\text{-}KIT^{neg}$ cells isolated from day 6 EBs that were cultured in the MEA (Multi ChannelSystems) dish for 2-3 weeks. Extracellular electrical activity was recorded with or without 1 μM quinidine (Sigma).
Figure 19:
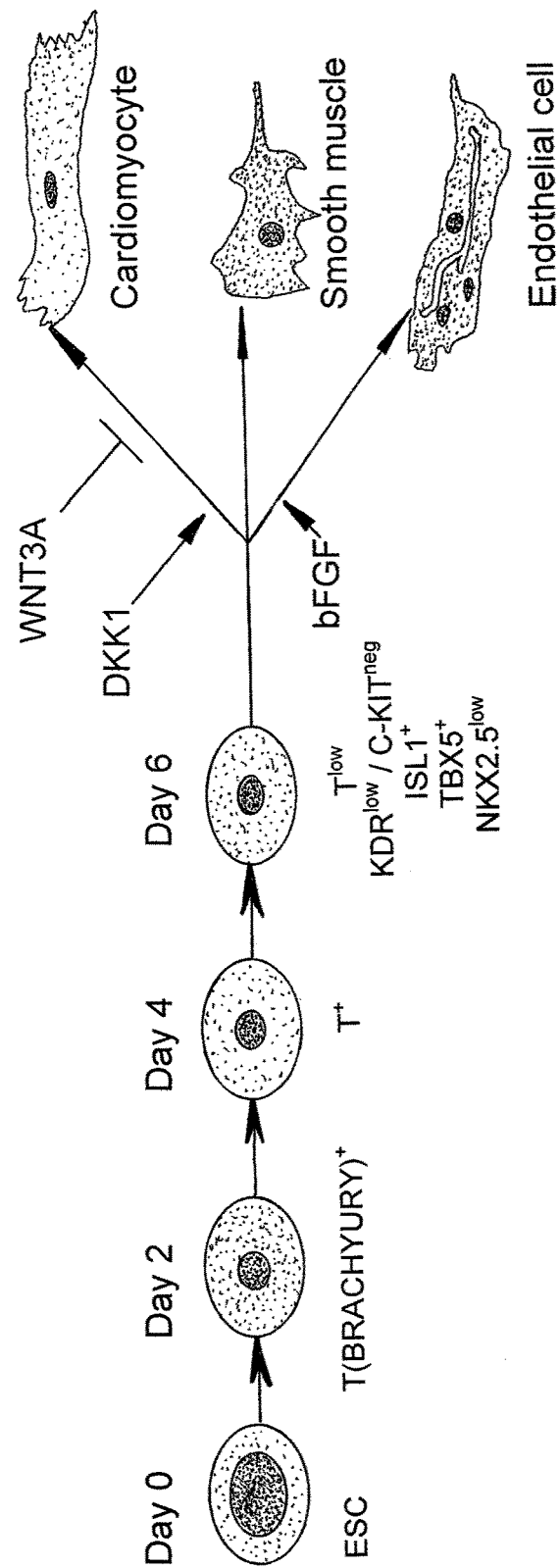
FIG. 19 is a model depicting development of the cardiovascular progenitors in hESC cultures.

Functional potential of $KDR^{low}/C\text{-}KIT^{neg}$-derived cardiomyocytes was evaluated with whole-cell current and field potential measurements. In whole-cell voltage clamp analysis, 80% of cells studied expressed a predominant voltage-gated, transient outward potassium current (FIGS. 15, 16). The voltage dependence, density and gating kinetics of this current (FIGS. 16, 17) resembled that of the $I_{to}$ potassium current found in human atrial and ventricular myocytes. Field potentials recorded from cultured cells using microelectrodes revealed that the human cardiovascular progenitors derived cardiac cells were electrically coupled to one another. In addition, as expected, the Vaugn Williams class Ia agent quinidine decreased the measured T wave amplitude and increased the QT interval (FIG. 19).

The invention claimed is:

1. An isolated population of human cardiovascular progenitor cells derived from human pluripotent stem cells in vitro, wherein the progenitor cells express KDR and do not express C-KIT and VE-CADHERIN and wherein the progenitor cells are progenitors of cardiomyocytes, endothelial cells, and vascular smooth muscle cells.

2. The population of human cardiovascular progenitor cells of claim 1 obtained by culturing human embryoid bodies in serum free media in the presence of activin and BMP.

3. The population of claim 2 wherein activin is activin A.

4. The population of claim 2 wherein BMP is BMP4.

5. A composition comprising the isolated population of human cardiovascular progenitor cells of claim 1.

* * * * *

SEQUENCE LISTING

<160> NUMBER OF SEQ ID NOS: 72

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
tgtcccaggt ggcttacaga tgaa                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtgtgccaa agttgccaat acac                                          24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aatgccactg catcttccac tggt                                          24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tggtgacagt tccttgctgt ctga                                          24

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tctcagtgtg gcacttacct gt                                            22

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccaagagatc cttgcgttct agact                                         25

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cctctactcc agtaaacctg attggg                                          26

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgttcccagc atttcacact atgg                                            24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cacaagcgtc tcgggattgt gttt                                            24

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agtggcaagt cttccgacaa                                                 20

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcgattatgc agcgtgcaat gagt                                            24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aacataaata cgggtgggtg cgtg                                            24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 13
gaaagaccac acagcctcat tgct                                          24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tcaatgtcag tgagcctgga ggaa                                          24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttctcggcca caagctggaa taca                                          24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
actgggtgga caggtaatgg ttgt                                          24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acctggtgga gttcaagacc atct                                          24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acctctacaa atgtggtatg gctg                                          24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
```
atcatttcta gcgcatggcc tggt                                          24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atttgtggag ggcgaggtca taga                                          24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tttgaatgat gagccttcgt cccc                                          24

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggtctcaagt cagtgtacag gtaagc                                        26

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aacctggagt ttgtgccagg gttt                                          24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgaacttcac cttccctcca acca                                          24

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
attcccagcc catgagtcct tga                                            23

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acacgtggaa caccaacatc ct                                             22

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aaggacgcac tgagcaacgc tatt                                           24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acgccactgt cacatccaca tagt                                           24

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aaatgaaacc cagcatagga gctggc                                         26

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acactcagcc tcacatctta ccct                                           24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttcaccaaag atctgctcct cgct                                           24

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ttattactgg tgtggagtgg gtgtgg                                        26

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acatcatcac ccacggagaa gaga                                          24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
attggaacat ggcctctgga tgga                                          24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tggagaagtg gcatcagtca acag                                          24

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tctacaatcc cttgcagtgt gag                                           23

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aatactctgt ctggatcggt ggct                                          24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
acgagtcaga gctttggcta ggaa                                          24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttgacctgaa ctcgtgcctt agga                                          24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggccttcagg ttgtttcttt ccgt                                          24

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cccatggtgg gttgtcatat attcatgt                                      28

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ccagcatcac atctcaaaca gcac                                          24

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tctatgacct cgccctccac aaa                                           23

-continued

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gaacggtgtc ttcaggttgg tatttca                                      27

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ttgtacggga tcaaatgcgc caag                                         24

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
aggccacaca gcggaaaca                                               19

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
acctcaacag ctccctgact ct                                           22

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ataatcgccg ccacaaactc tcc                                          23

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gtctctcagc tcctgggtat catctt                                       26

<210> SEQ ID NO 50

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgttgctatg gatgctgtgc tggt                                           24

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tggaagcgtg tgaagggagg t                                              21

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aaggaagagg gtgaaggtgg gattg                                          25

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
agttcagctc cttccaccac aac                                            23

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cgtttcatac tcctcatcct ccactatcc                                      29

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tcgaagggcc aaatggagaa gagaag                                         26

<210> SEQ ID NO 56
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggtgggttgt ggaattggtt ggtaga                                          26

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cctgtgtgta ccctggagtt tctgt                                           25

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tgcacgaagc acctgcaata agatg                                           25

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tgtcagtaaa cgggcaggta ctca                                            24

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ataccatcct tccgcatggt cagt                                            24

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aggaaatcct cagactcctg ggtt                                            24

<210> SEQ ID NO 62
<211> LENGTH: 24
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 62
cccaaactgt tcaagtggca gaca                                          24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gcattcccaa tcttgacacg gtga                                          24

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gcccttgcag ccagaataca catt                                          24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ttggccatgt cgtcaccatt ctct                                          24

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cccacaccct aaccagcctt t                                             21

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
actttggaag acagaaccaa attatctc                                      28

<210> SEQ ID NO 68
<211> LENGTH: 17
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 68
tgggcaccat tccacca                                                        17

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cagtggcagt ctcaggttaa gaagga                                              26

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cgctactgca ggtgtgagca a                                                   21

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gaagagtgcg atcaagaacc catgac                                              26

<210> SEQ ID NO 72
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gtctctcctc cttctcctcc tatctttact t                                        31
```